(12) United States Patent
Seed et al.

(10) Patent No.: US 8,748,419 B2
(45) Date of Patent: Jun. 10, 2014

(54) TREATING OBESITY WITH MUSCARINIC RECEPTOR $M_1$ ANTAGONISTS

(75) Inventors: Brian Seed, Boston, MA (US); Jordan Mechanic, Sunnyvale, CA (US)

(73) Assignee: Theracos, Inc., Marlborough, MA (US)

( * ) Notice: Subject to any disclaimer, the term of this patent is extended or adjusted under 35 U.S.C. 154(b) by 0 days.

(21) Appl. No.: 11/763,313

(22) Filed: Jun. 14, 2007

(65) Prior Publication Data
US 2007/0293481 A1 Dec. 20, 2007

Related U.S. Application Data

(60) Provisional application No. 60/805,066, filed on Jun. 16, 2006, provisional application No. 60/829,225, filed on Oct. 12, 2006.

(51) Int. Cl.
*C07D 487/04* (2006.01)
*A61K 31/55* (2006.01)
*C07D 333/20* (2006.01)
*C07D 307/80* (2006.01)
*A61K 31/135* (2006.01)

(52) U.S. Cl.
USPC ........... 514/220; 514/221; 514/438; 514/469; 514/649; 514/657

(58) Field of Classification Search
None
See application file for complete search history.

(56) References Cited

U.S. PATENT DOCUMENTS

| | | | |
|---|---|---|---|
| 5,344,832 A | 9/1994 | Cincotta et al. | |
| 5,436,272 A | 7/1995 | Scheinbaum | |
| 5,585,347 A | 12/1996 | Meier et al. | |
| 5,597,797 A * | 1/1997 | Clark | 514/12 |
| 5,668,155 A * | 9/1997 | Cincotta et al. | 514/340 |
| 5,700,795 A | 12/1997 | Cincotta | |
| 5,712,265 A | 1/1998 | Cincotta et al. | |
| 5,795,895 A * | 8/1998 | Anchors | 514/253.04 |
| 6,403,657 B1 * | 6/2002 | Hinz | 424/682 |
| 6,703,383 B2 | 3/2004 | Wu et al. | |

(Continued)

FOREIGN PATENT DOCUMENTS

CA 2193530 A1 12/1995
CN 101472571 B 11/2012

(Continued)

OTHER PUBLICATIONS

Bernard Testa, Prodrug Research: Futile or Fertile?, 68 Biochem. Pharmacol. 2097 (2004.*

(Continued)

*Primary Examiner* — Ernst Arnold
*Assistant Examiner* — Kyung Sook Chang
(74) *Attorney, Agent, or Firm* — Kilpatrick Townsend & Stockton LLP

(57) ABSTRACT

Provided are methods of treating obesity and effecting desired weight loss or preventing undesired weight gain by administration of a preferential muscarinic acetylcholine receptor $M_1$ antagonist, optionally with at least one antidepressant other than a selective muscarinic acetylcholine receptor $M_1$ antagonist. The preferential muscarinic acetylcholine receptor $M_1$ antagonist, optionally can be administered with an anti-obesity agent, for example, an anorexiant. The invention also provides for pharmaceutical compositions and kits for administration of at least one selective muscarinic acetylcholine receptor $M_1$ antagonist in combination with at least one antidepressant other than a selective muscarinic acetylcholine receptor $M_1$ antagonist.

10 Claims, 15 Drawing Sheets

(56) References Cited

U.S. PATENT DOCUMENTS

| | | | |
|---|---|---|---|
| 6,803,357 B1 | 10/2004 | Bachovchin et al. | |
| 6,872,716 B2 | 3/2005 | Wu et al. | |
| 7,109,198 B2 | 9/2006 | Gadde et al. | |
| 2004/0204472 A1* | 10/2004 | Briggs et al. | 514/406 |
| 2005/0143350 A1* | 6/2005 | Seed | 514/114 |
| 2005/0227998 A1 | 10/2005 | Voelker | |
| 2006/0073217 A1* | 4/2006 | Barak | 424/722 |

FOREIGN PATENT DOCUMENTS

| | | |
|---|---|---|
| JP | 2009-530697 | 8/2009 |
| WO | WO 95/35110 | 12/1995 |
| WO | WO 99/13877 A1 | 3/1999 |
| WO | WO 99/43647 A1 | 9/1999 |
| WO | WO 00/10551 A2 | 3/2000 |
| WO | WO 2005/051297 A2 | 6/2005 |
| WO | 2006/017614 | 2/2006 |
| WO | WO 2006/127418 A1 | 11/2006 |
| WO | 2007/147123 | 12/2007 |

OTHER PUBLICATIONS

W. Londong, et al, Telenzepine is at Least 25 Times More Potent Than Pirenzepine—A Dose Response and Comparative Secretory Study in Man, 28 GUT 888 (1987).*

Thomas A. Wadden et al, Effects of Sibutramine Plus Orlistat in Obese Women Following 1 Year of Treatment by Sibutramine Alone: A Placebo-Controlled Trial, 8 Obesity Res. 431 (Sep. 2000).*

Thomas Wadden, et al, Effects of Sibutramine Plus Orlistat in Obese Women Following 1 Year Treatment by Sibutramine Alone: A Placebo-Controlled Trial, 8 Obesity Res. 431 (Sep. 2000).*

Bevan, J., et al., "Cholinergic blockade with pirenzepine induces dose-related reduction in glucose and insulin responses to a mixed meal in normal subjects and non-insulin dependent diabetics," *Clinical Endocrinology*, vol. 35, pp. 85-91 (1991).

Chau, D.T., et al., "Nucleus accumbens muscarinic receptors in the control of behavioral depression: antidepressant-like effects of local $M_1$ antagonist in the Porsolt swim test," *Neuroscience*, vol. 104(3), pp. 791-798 (Jun. 2001).

Hammer, R., et al., "The pharmacokinetic profile of pirenzepine," *Scand. J. Gastroenterol. Suppl.*, vol. 57, pp. 1-6 (1979).

Miyakawa, T., et al., "Hyperactivity and intact hippocampus-dependent learning in mice lacking the $M_1$ muscarinic acetylcholine receptor," *The Journal of Neuroscience*, vol. 21(14), pp. 5239-5250 (Jul. 2001).

Rogóż, Z, et al., "Central Action of Pirenzepine," *Pol. J. Pharmacol. Pharm.*, vol. 33, pp. 615-626 (1981).

Trummlitz, G., et al., "Conformational analysis of the antiulcer drug pirenzepine. X-ray investigations, molecular mechanics and quantum mechanical calculations and comparisons with structurally or pharmacologically related compounds " *Arzneimittelforschung*, vol. 34(8), pp. 849-859 (1984).

Longdong, et al., "Telenzepine is at Least 25 Times More Potent Than Pirenzepine—A Dose Response and Comparative Secretory Study in Man," 28 GUT 888 (1987).

Muratori, F., et al., "Accute Cholinergic Blockade with Pirenzepine Reduces the Insulin and Glucose Responses to Oral Glucose Test in Obese Women," *International Journal of Obesity*, Newman Pub., London, GB, vol. 28, No. Suppl. 1, Apr. 1, 2004, p, S221.

Gouret, et al., "Biochemical and pharmacological evaluation of the novel antidepressant and serotonin uptake inhibitor 2-(3, 4-Dicholoobenzyl)-2-dimethylamino-1-propanol hydrochloride," http://www.ncbi.nlm.nih.gov;pubmed/2168703, Institut de Recherche Jouveinal, Arzneimittelforschung, 1990, No. 40(6), p. 633-40.

Table 17-1, *Goodman & Gilman's The Pharmacological Basis of Therapeutics*, 11th Edition, Brunton, Lazo and Parker, Eds., McGraw-Hill (2006), p. 434.

Appolinario, et al., "Psychotropic Drugs in Treatment of Obesity," *CNS Drugs* (2004) 18(10):629-51.

Campfield et al., "Strategies and Potential Molecular Targets for Obesity Treatment," *Science* 280, 1383-1387 (1998).

Cascade, et al., "Real-World Data on SSRI Antidepressant Side Effects," *Psychiatry*(Edgemont), 2009;6(2):16-18.

Fava, et al., "Fluoxetine Versus Sertraline and Paroxetime in Major Depressive Disorder: Changes in Weight With Long-Term Treatment," *J Clin Psychiatry* 61:11, Nov. 2000, 863-867.

Greenway, et al., "Rational Design of a Combination Medication for the Treatment of Obesity," *Obesity*, (Silver Spring), Jan. 2009;17(1):30-9.

Halford, et al., "Serotonergic Drugs—Effects on Appetite Expression and Use for the Treatment of Obesity," *Drugs* (2007) 67(1):27-55.

Herremans, et al., "Effects of Infusion of Cholinergic Drugs into the Prefrontal Cortex Area on Delayed Matching to Position Performance in the Rat," *Brain Research* 711 (1996) 102-111.

Jia, et al., "Mechanism of Drug Combinations: Interaction and Network Perspectives," *Nature Reviews—Drug Discovery* (2009) 8:111-128.

Korner et al., "Pharmacological Approaches to Weight Reduction: Therapeutic Targets," *J. Clin. Endocrinol. Metab.*, 2004 89: 2616-2621.

Li, et al., "N-Desmethylclozapine, a Major Metabolite of Clozapine, Increases Cortical Acetylcholine and Dopamine Release In Vivo via Stimulation of $M_1$ Muscarinic Receptors," *Neuropsychopharmacology* (2005) 30:1986-1995.

Li et al., "Meta-Analysis: Pharmacologic Treatment of Obesity," *Ann. Intern. Med.* 2005:142:532-546.

Maina, et al., "Weight Gain During Long-Term Treatment of Obsessive-Compulsive Disorder: A Prospective Comparison Between Serotonin Reuptake Inhibitors," *J Clin Psychiatry* 65:10 Oct. 2004, 1365-1371.

Maslanski, et al., "Assesment of the Muscarinic Receptor Subtypes Involved in Pilocarpine-Induced Seizures in Mice," *Neuroscience Letters*, 168 (1994) 225-228.

Mayorga, et al., "Characterization of the Muscarinic Receptor Subtype Mediating Pilocarpine-Induced Tremulous Jaw Movements in Rats," *European Journal of Pharmacology*, 364 (1999) 7-11.

Power, et al., "Cholinergic Modulation of Memory in the Basolateral Amygdala Involves Activation of both M1 and M2 Receptors," *Behavioural Pharmacology* 2003 14:207-213.

Quinn, "Comparing Rat's to Human's Age: How Old is my Rat in People Years," Nutrition (2005), 21:775-777.

Sansone, et al., "Naturalistic Study of the Weight Effects of Amitriptyline, Fluoxetine, and Sertraline in an Outpaient Medical Setting," *J Clinical Psychopharmacol* (2000) 20(2): 272-4.

Valentino et al., "Central and Peripheral Molecular Targets for Antiobesity Pharmacotherapy," *Nature Publishing*, vol. 87, No. 6, Jun. 2010, 652-662.

Wadden, et al., "Sertraline and Relapse Prevention Training Following Treatment by Very-Low-Calorie Diet: A Controlled Clinical Trial," *Obesity Res* (1995) 3(6):549-557.

Jackson et al., "Comparison of the effects of sibutramine and other monoamine reuptake inhibitors on food intake in the rat," J. Pharmacol, 1997, vol. 121, No. 8, pp. 1758-1762.

Mancini et al., "Pharmacological treatment of obesity," Arq Bras Endocrinol Metabol., 2006, vol. 50, No. 2, pp. 377-389.

* cited by examiner

TREATING OBESITY WITH MUSCARINIC RECEPTOR M₁ ANTAGONISTS

CROSS-REFERENCE TO RELATED APPLICATIONS

This application claims the benefit of U.S. Provisional Application No. 60/805,066, filed Jun. 16, 2006 and U.S. Provisional Application No. 60/829,225, filed Oct. 12, 2006, the entire disclosures of both of which are hereby incorporated herein by reference.

STATEMENT AS TO RIGHTS TO INVENTIONS MADE UNDER FEDERALLY SPONSORED RESEARCH AND DEVELOPMENT

Not Applicable

FIELD OF THE INVENTION

The present invention relates to the treatment of obesity and the facilitation of weight loss by administration of a selective $M_1$ muscarinic receptor ($M_1R$) antagonist, alone or in combination with an antidepressant.

BACKGROUND OF THE INVENTION

The neurotransmitter acetylcholine (ACh) interacts with two types of receptors in effector cell membranes: nicotinic receptors (nAChR), which are ligand-gated ion channels, and muscarinic receptors (mAChR), which are G protein-coupled receptors. In mammals five subtypes of mAChR, designated $M_1$ to $M_5$, have been identified. The $M_1$ muscarinic receptor ($M_1R$) is found in both the central and peripheral nervous systems, particularly the cerebral cortex and sympathetic ganglia. The muscarinic effects mediated by $M_1R$ have been studied largely by use of $M_1R$-selective antagonists and, more recently, by the development of $M_1R$-null mice.

Although no currently known mAChR antagonists display absolute selectivity for a single muscarinic receptor subtype, the drugs pirenzepine and telenzepine exhibit high relative affinity for $M_1R$ and are therefore often considered $M_1R$-selective. Pirenzepine is used to treat peptic ulcer disease in Europe, Japan and Canada. Telenzepine has been tested in clinical trials for the same indication. At therapeutic doses, they moderately reduce gastric acid and pepsin secretion without inhibiting smooth muscle activity as do non-selective mAChR antagonists.

There are several lines of evidence suggesting that the $M_1R$ subtype may be involved in certain aspects of depressive disorders and anxiety. Direct injection of pirenzepine into the nucleus accumbens in the forebrain of rats resulted in increased swimming time in the Porsolt swim test (see, Chau, D. T., et al., *Neuroscience*, 2001, vol. 104, no. 3, pp. 791-8), a common measure of antidepressant activity. $M_1R$-null mice also displayed increased swimming time in the Porsolt swim test, as well as increased social contacts in a social interaction test (see, Miyakawa, T., et al., *J. Neurosci.*, 2001, vol. 21, no. 14, pp. 5239-50).

While pirenzepine and telenzepine are structurally similar to tricyclic antidepressants such as imipramine, they are not known to have psychotropic effects when taken orally for the treatment of peptic ulcer disease. In addition, in earlier studies of mice and rats, pirenzepine administered systemically failed to elicit any behavioral effects (see, Rogoz, Z., Skuza, G., Sowinska, H., *Pol. J. Pharmacol. Pharm.*, 1981, vol. 31, pp. 615-26). The lack of such effects can be explained by the observation that pirenzepine does not exhibit significant penetration of the blood-brain barrier in various species, including rodents and humans (see, Hammer, R., Koss, F. W., *Scand. J. GastroenteroL, Suppl.*, 1979, vol. 14, no. 57, pp. 1-6; Bymaster, F. P., et al., *J. Pharmacol. Exp. Ther.*, 1993, vol. 267, no. 1, pp. 16-24). It is for that reason that the above-mentioned study of the effect of pirenzepine in the Porsolt swim test utilized direct injection of the drug into the brain of test animals.

Others have also disclosed using selective $M_1R$ antagonists for altering lipid metabolism and for reducing body fat stores. See, e.g. U.S. Pat. No. 5,668,155. However, it was required to administer the $M_1R$ antagonists at a predetermined time in a 24-hour period to achieve desired results. Further, Bevan, et al., *Clinical Endocrinology* (1991) 36:85-91 disclose administering pirenzepine to non-obese and obese human patients diagnosed with non-insulin dependent diabetes (NIDDM). Bevan related the timing of administration of pirenzepine with the timing of a meal, but does not disclose or suggest the ability of pirenzepine to interfere with lipogenic sensitivity or its use in facilitating weight loss.

There exists a need for new and effective medications for the treatment of obesity and for facilitating weight loss. The present invention addresses this and other needs.

BRIEF SUMMARY OF THE INVENTION

The present invention provides methods for treating obesity, suppressing appetite, facilitating or promoting weight loss, facilitating or promoting maintenance of a desired weight, and preventing or decreasing undesired weight gain, by administering a therapeutically effective amount of one or more $M_1R$-selective antagonists. In practicing the present methods, the one or more $M_1R$-selective antagonists can be administered without other pharmacological agents or in combination with other pharmacological agents, for example, one or more antidepressants other than a $M_1R$-selective antagonist. In some embodiments, one or more $M_1R$-selective antagonists can be co-administered with one or more anti-obesity agents. In some embodiments, one or more $M_1R$-selective antagonists combined with one or more antidepressants other than a $M_1R$-selective antagonist can be co-administered with one or more anti-obesity agents.

The one or more $M_1R$-selective antagonists need not be administered at a predetermined time in a 24-hour period. Efficacious results can be achieved without correlating the administration of the one or more $M_1R$-selective antagonists with a peak or nadir in a circadian oscillation of a hormone. The administration of the one or more $M_1R$-selective antagonists need not be correlated with a particular time of day or with a meal. In some embodiments, the administration of the one or more $M_1R$-selective antagonists is timed to correlate with a meal, for example, before, during or after a meal.

Accordingly, in a first aspect, the invention provides methods for promoting weight loss or facilitating maintenance of a stable weight, the method comprising administering to an obese or overweight individual in need thereof a therapeutically effective amount of one or more $M_1R$-selective antagonists to effectuate weight loss, whereby weight loss is promoted or maintenance of a stable weight is facilitated.

In another aspect, the invention provides pharmaceutical compositions comprising a mixture of therapeutically effective amounts of one or more $M_1R$-selective antagonists and one or more antidepressants other than a $M_1R$-selective antagonist. In some embodiments, the pharmaceutical compositions comprise a mixture of therapeutically effective amounts of one or more $M_1R$-selective antagonists and one or more anti-obesity agents. In some embodiments, the pharmaceutical compositions comprise a mixture of therapeutically effective amounts of one or more $M_1R$-selective antagonists, one or more antidepressants other than a $M_1R$-selective antagonist, and one or more anti-obesity agents.

In another aspect, the invention provides kits comprising a mixture of therapeutically effective amounts of one or more $M_1R$-selective antagonists and one or more antidepressants other than a $M_1R$-selective antagonist. In some embodiments, the kits comprise a mixture of therapeutically effective amounts of one or more $M_1R$-selective antagonists and one or more anti-obesity agents. In some embodiments, the kits comprise a mixture of therapeutically effective amounts of one or more $M_1R$-selective antagonists, one or more antidepressants other than a $M_1R$-selective antagonist, and one or more anti-obesity agents.

With regard to the embodiments for carrying out the methods, and for the pharmaceutical compositions and kits, in one embodiment, the one or more $M_1R$-selective antagonists is selected from the group consisting of pirenzepine, telenzepine, and combinations thereof. In one embodiment, the $M_1R$-selective antagonist is telenzepine (racemic or an optical isomer). In one embodiment, the $M_1R$-selective antagonist is pirenzepine.

In one embodiment, the one or more $M_1R$-selective antagonists are administered without a second pharmacological agent.

In one embodiment, the one or more $M_1R$-selective antagonists is administered in combination with or combined with one or more antidepressants other than a $M_1R$-selective antagonist. In one embodiment, the antidepressant is selected from the group consisting of a selective serotonin reuptake inhibitor (SSRI) and a selective serotonin-norepinephrine reuptake inhibitor (SNRI).

In one embodiment, the antidepressant is a SSRI. In one embodiment, the SSRI is selected from the group consisting of citalopram, escitalopram, fluoxetine, fluvoxamine, paroxetine and sertraline. In one embodiment, the SSRI is selected from the group consisting of citalopram, sertraline, paroxetine, and fluoxetine.

In one embodiment, the antidepressant is a SNRI. In one embodiment, the SNRI is selected from the group consisting of milnacipran, mirtazapine, venlafaxine, duloxetine, desvenlafaxine and sibutramine. In one embodiment, the SNRI is venlafaxine.

The methods achieve efficacious results without requiring the administration of an anti-obesity agent, for example, without requiring administration of an anorexiant. However, in some embodiments, the one or more $M_1R$-selective antagonists is administered in combination with or combined with one or more anti-obesity agents, for example, one or more anorexiants.

Furthermore, efficacious results can be achieved without timed administration of the one or more $M_1R$-selective antagonists. Co-administered active agents, including antidepressants, anti-obesity agents and anorexiants also provide efficacious results without timed administration.

In one embodiment, the one or more $M_1R$-selective antagonists is telenzepine (racemic or an optical isomer) and the one or more antidepressants other than a $M_1R$-selective antagonist is fluoxetine (racemic or an optical isomer).

In one embodiment, the one or more $M_1R$-selective antagonists is telenzepine (racemic or an optical isomer) and the one or more antidepressants other than a $M_1R$-selective antagonist is fluvoxamine.

In one embodiment, the one or more $M_1R$-selective antagonists is telenzepine (racemic or an optical isomer) and the one or more antidepressants other than a $M_1R$-selective antagonist is sertraline or its S-enantiomer, Zoloft®.

In one embodiment, the one or more $M_1R$-selective antagonists is telenzepine (racemic or an optical isomer) and the one or more antidepressants other than a $M_1R$-selective antagonist is citalopram (or escitalopram).

In one embodiment, the one or more $M_1R$-selective antagonists is telenzepine (racemic or an optical isomer) and the one or more antidepressants other than a $M_1R$-selective antagonist is paroxetine.

In one embodiment, the one or more $M_1R$-selective antagonists is telenzepine (racemic or an optical isomer) and the one or more antidepressants other than a $M_1R$-selective antagonist is venlafaxine (racemic or an optical isomer).

In one embodiment, the one or more $M_1R$-selective antagonists is telenzepine (racemic or an optical isomer) and the one or more antidepressants other than a $M_1R$-selective antagonist is desvenlafaxine.

In one embodiment, the one or more $M_1R$-selective antagonists is telenzepine (racemic or an optical isomer) and the one or more antidepressants other than a $M_1R$-selective antagonist is duloxetine.

In one embodiment, the one or more $M_1R$-selective antagonists is telenzepine (racemic or an optical isomer) and the one or more antidepressants other than a $M_1R$-selective antagonist is sibutramine.

In one embodiment, the one or more $M_1R$-selective antagonists is telenzepine (racemic or an optical isomer) and the one or more antidepressants other than a $M_1R$-selective antagonist is milnacipran.

In one embodiment, the one or more $M_1R$-selective antagonists is telenzepine (racemic or an optical isomer) and the one or more antidepressants other than a $M_1R$-selective antagonist is mirtazapine.

In one embodiment, the one or more $M_1R$-selective antagonists is telenzepine (racemic or an optical isomer) and the one or more antidepressants other than a $M_1R$-selective antagonist is bupropion.

In one embodiment, the one or more $M_1R$-selective antagonists is telenzepine (racemic or an optical isomer) and the one or more anti-obesity agents is phentermine.

In a related aspect, the invention provides methods for preparing or use of a medicament for treating obesity, suppressing appetite, facilitating or promoting weight loss, facilitating or promoting maintenance of a desired weight, and preventing or decreasing undesired weight gain, the medicament containing a therapeutically effective amount of one or more $M_1R$-selective antagonists. The medicament can optionally also contain one or more antidepressants other than a $M_1R$-selective antagonist. The medicament can optionally also contain one or more anti-obesity agents. The embodiments for the medicament are as described herein.

In some embodiments, the methods and compositions of the invention comprise the combinations of pharmacological agents set forth herein. In some embodiments, the methods and compositions of the invention consist essentially of the combinations of pharmacological agents set forth herein.

DEFINITIONS

The term "obese" or "obesity" refers to an individual who has a body mass index (BMI) of 30 kg/m$^2$ or more due to excess adipose tissue. Obesity also can be defined on the basis of body fat content: greater than 25% body fat content for a male or more than 30% body fat content for a female. A "morbidly obese" individual has a body mass index greater than 35 kg/m$^2$.

The term "overweight" refers to an individual who has a body mass index of 25 kg/m$^2$ or more, but less than 30 kg/m$^2$.

The term "body mass index" or "BMI" refers to a weight to height ratio measurement that estimates whether an individual's weight is appropriate for their height. As used herein, an individual's body mass index is calculated as follows:

BMI=(pounds×700)/(height in inches)$^2$ or

BMI=(kilograms)/(height in meters)$^2$

The term "baseline body weight" refers to the body weight presented by the individual at the initiation of treatment.

As used herein, "administering" means oral ("po") administration, administration as a suppository, topical contact, intravenous ("iv"), intraperitoneal ("ip"), intramuscular ("im"), intralesional, intranasal or subcutaneous ("sc") administration, or the implantation of a slow-release device e.g., a mini-osmotic pump, to a subject. Administration is by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration, with the proviso that, as used herein, systemic administration does not include direct administration to the brain region by means other than via the circulatory system, such as intrathecal injection and intracranial administration.

The term "co-administer" refers to the simultaneous presence of two active agents in the blood of an individual. Active agents that are co-administered can be concurrently or sequentially delivered.

As used herein, the terms "treating" and "treatment" refer to delaying the onset of, retarding or reversing the progress of, or alleviating or preventing either the disease or condition to which the term applies, or one or more symptoms of such disease or condition.

As used herein, the terms "selective muscarinic receptor M$_1$ antagonist" and "M$_1$R-selective antagonist" refer to a muscarinic acetylcholine receptor antagonist that exhibits preferential interaction with the muscarinic receptor M$_1$ subtype in comparison to the muscarinic receptor subtypes M$_2$ and M$_3$. Exemplified M$_1$R-selective antagonists include, but are not limited to, pirenzepine and telenzepine. Preferential binding need not be complete. For example, despite comparable affinities for M$_1$ and M$_4$ receptor subtypes, pirenzepine is classified as an M$_1$R-selective antagonist.

Preferential binding of a M$_1$R-selective antagonist can be measured in a competitive displacement assay. A M$_1$R-selective antagonist will preferentially displace a known M$_1$R-selective ligand (e.g. pirenzepine and/or telenzepine) in comparison to known M$_2$ (e.g. tripitramine, himbacine, methoctramine) and M$_3$ (e.g. darifenacin, hexahydrosiladiphenidol) selective ligands. Alternatively, a M$_1$R-selective antagonist will preferentially displace a nonselective muscarinic ligand (e.g., quinuclidinyl benzilate (QNB), N-methylscopolamine (NMS)) from an M$_1$ receptor subtype in comparison to displacing the non-selective muscarinic ligand from binding to the M$_2$ and M$_3$ receptor subtypes. The relative potencies for displacement of radiolabeled competitors can be expressed in terms of the concentration at which 50% of the competitor is displaced (IC$_{50}$), or in terms of an equilibrium dissociation constant (K$_d$). The IC$_{50}$ value and/or the equilibrium dissociation constant can be calculated using available software by entering the values of detected labeled ligand in the presence of titrated amounts of unlabeled test compound (e.g., LIGAND (Munson, P. J., and Rodbard, D., *Anal. Biochem.* (1980) 107:220-39 or DATAPLOT, National Technical Information Services). A M$_1$R-selective antagonist will have an IC$_{50}$ value or a K$_d$ value for binding to an M$_1$ receptor subtype that is at least about 3-fold less, preferably at least about 10-fold less, and more preferably at least about 30-fold less than its IC$_{50}$ value or K$_d$ value for binding to M$_2$ and M$_3$ receptor subtypes. Applicable radioligand binding assays, using radiolabeled NMS or QNB, are disclosed in Buckley, et al., *Molecular Pharmacology* (1989) 35:469-76 and Bolden, et al, *J Pharmacol Exp Ther*. (1992) 260:576-80.

As used herein, the term "anti-obesity agent" refers to a pharmaceutical agent whose primary purpose is to effect weight loss. Exemplary anti-obesity agents include, without limitation, anorexiants, dopamine agonists, H$_3$-histamine antagonists, 5-HT2c receptor agonists, beta-3 adrenergic receptor agonists, cholecystokinin agonists, anti-epileptic agents, leptin, leptin analogs and leptin receptor agonists, neuropeptide Y (NPY) receptor antagonists and modulators, peptide-YY (PYY) receptor agonists, ciliary neurotrophic factor, thyroid hormone receptor-beta agonists, cannabinoid CB1 receptor antagonists, melanin-concentrating hormone receptor antagonists, pancreatic and gastric lipase inhibitors, melanocortin-4 receptor agonists, and combinations thereof. As used herein, the term "anti-obesity agent" specifically excludes M$_1$R selective muscarinic antagonists and antidepressants.

As used herein, the term "anorexiant" or "anorectic" interchangeably refer to a pharmaceutical agent whose primary intended effect is the suppression of appetite. Anorexiants include, but are not limited to, the sympathomimetic amines. The sympathomimetic amines are well known and discussed in detail in, for example, *Goodman and Gilman's The Pharmacological Basis of Therapeutics*, 11$^{th}$ Ed., Brunton, Lazo and Parker, Eds., McGraw-Hill (2006), Chapter 10, pp. 237-263, hereby incorporated herein by reference. As used herein, the terms "anorexiant" or "anorectic" specifically exclude M$_1$R selective muscarinic antagonists and antidepressants.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than a M$_1$R-selective antagonist and an antidepressant. In some embodiments, additional active agents that can be excluded include one or more of a prolactin inhibitor, a prolactin stimulator, a 5-HT receptor antagonist, a 5-HT receptor agonist, a NK-1 receptor antagonist and/or a dipeptidylpeptidase IV inhibitor.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of pharmacy*, 21st Ed., Lippencott Williams & Wilkins (2006). As discussed therein, immediate and nonimmediate release can be defined kinetically by reference to the following equation:

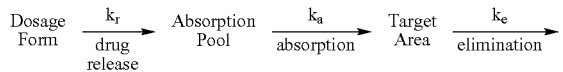

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

DETAILED DESCRIPTION

1. Introduction

Figure 1:
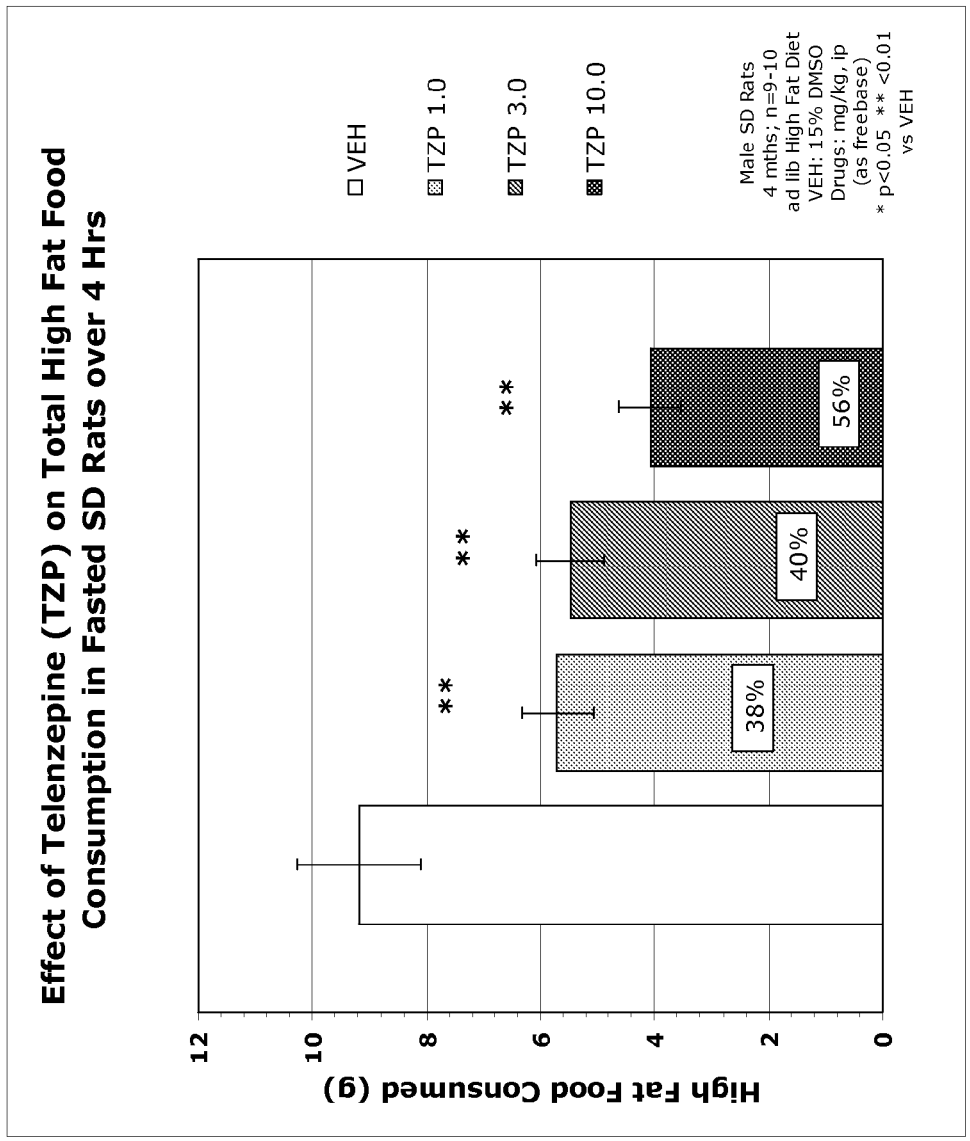
FIG. 1 illustrates the effect of telenzepine (TZP) on total high fat food consumption in fasted rats over 4 hours. Four-month old male Sprague-Dawley rats (n=9-10 per group) were administered intraperitoneally telenzepine in doses of 1.0 mg/kg, 3.0 mg/kg or 10.0 mg/kg, as described in the Examples below. All active agents were delivered in free base form. Control rats (VEH) were administered 15% DMSO. * indicates p<0.05 vs. VEH. ** indicates p<0.01 vs. VEH.
Figure 2:
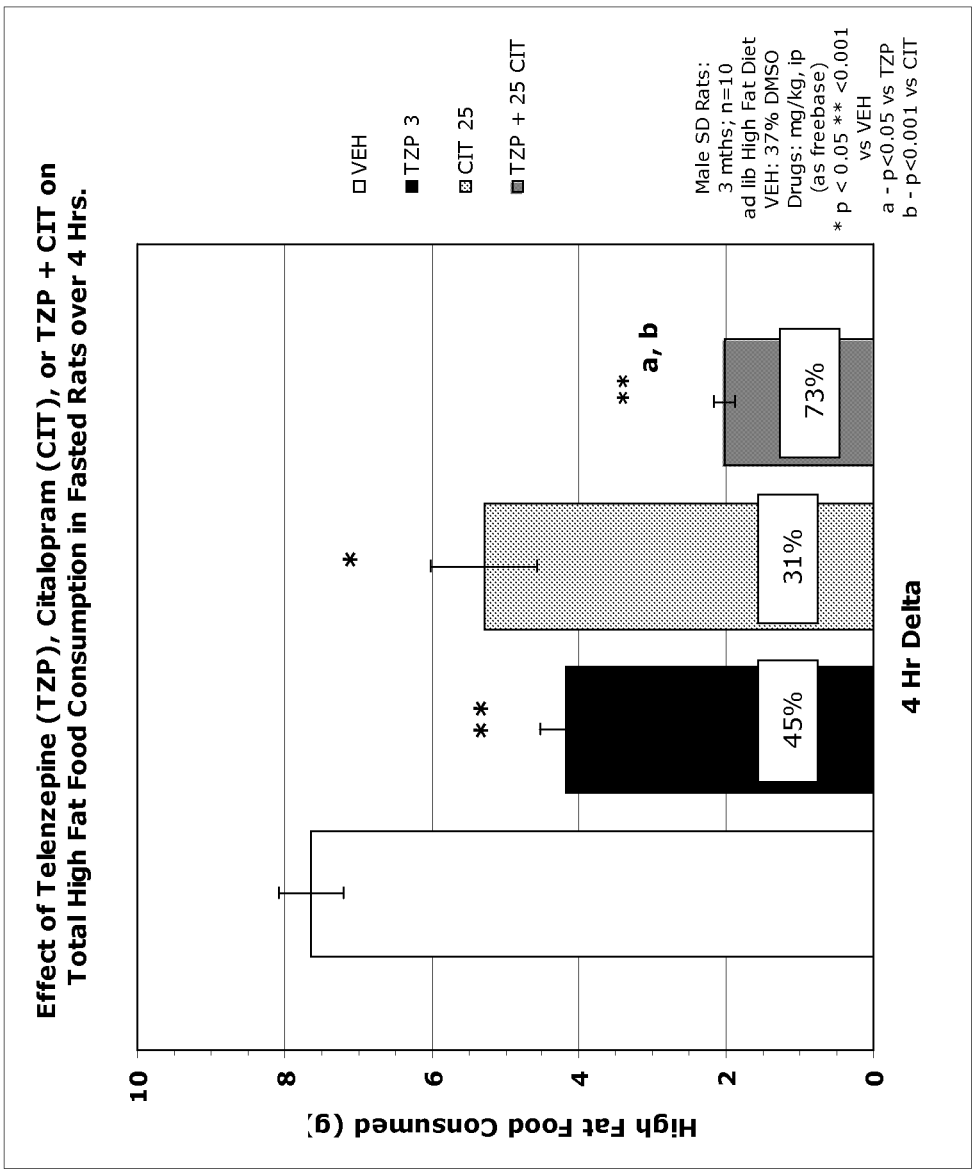
FIG. 2 illustrates the effect of telenzepine (TZP) alone, citalopram (CIT) alone and combined telenzepine and citalopram on total high fat food consumption in fasted rats over 4 hours. Three-month old male Sprague-Dawley rats (n=10 per group) were administered intraperitoneally telenzepine alone (3 mg/kg), citalopram alone (25 mg/kg), or co-administered telenzepine (3 mg/kg) and citalopram (25 mg/kg), as described in the Examples below. All active agents were delivered in free base form. Control rats (VEH) were administered 37% DMSO. * indicates p<0.05 vs. VEH. ** indicates p<0.001 vs. VEH. "a" indicates p<0.05 vs. TZP. "b" indicates p<0.001 vs. CIT.
Figure 3:
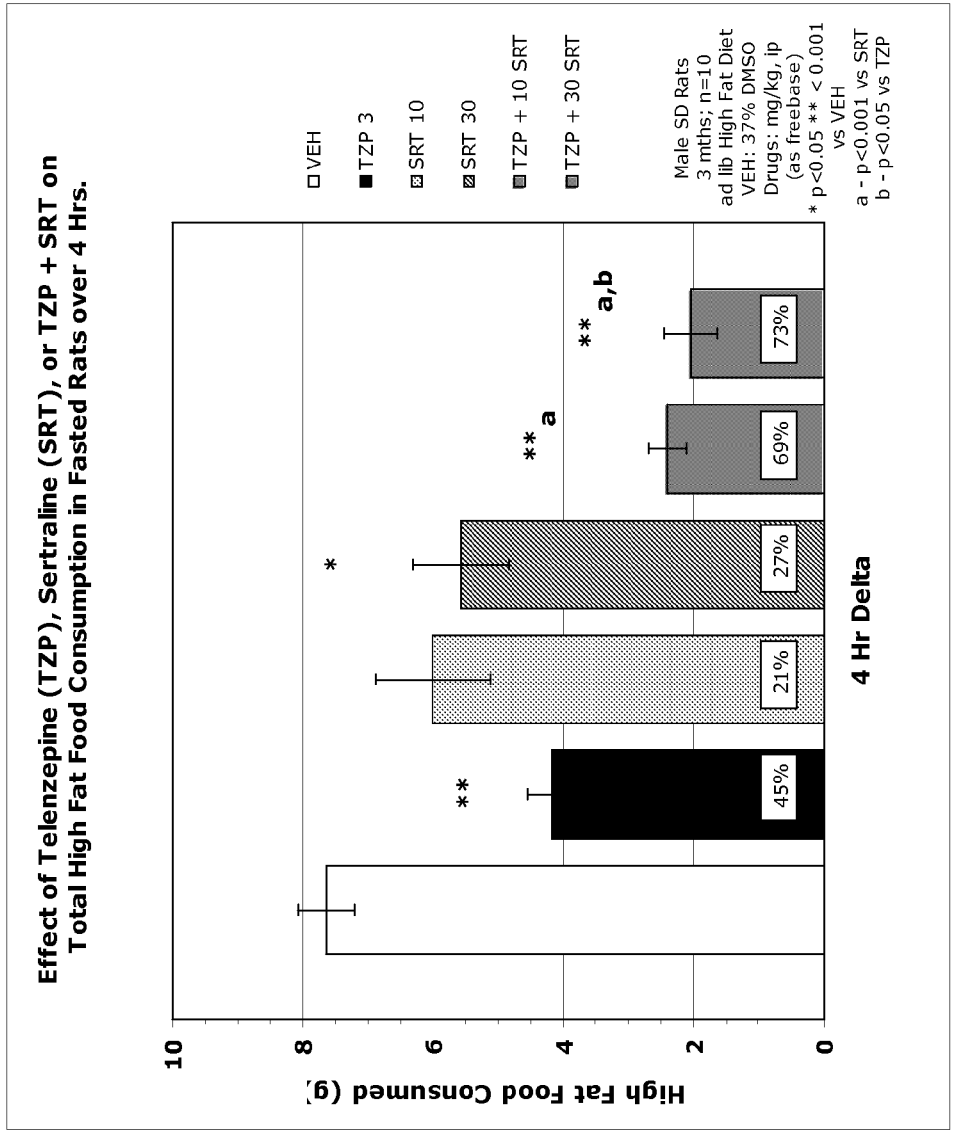
FIG. 3 illustrates the effect of telenzepine (TZP) alone, sertraline (SRT) alone and combined telenzepine and sertraline on total high fat food consumption in fasted rats over 4 hours. Three-month old male Sprague-Dawley rats (n=10 per group) were administered intraperitoneally telenzepine alone (3 mg/kg), sertraline alone (10 mg/kg or 30 mg/kg), or co-administered telenzepine (3 mg/kg) and sertraline (10 mg/kg or 30 mg/kg), as described in the Examples below. All active agents were delivered in free base form. Control rats (VEH) were administered 37% DMSO. * indicates p<0.05 vs. VEH. ** indicates p<0.001 vs. VEH. "a" indicates p<0.001 vs. SRT. "b" indicates p<0.05 vs. TZP.
Figure 4:
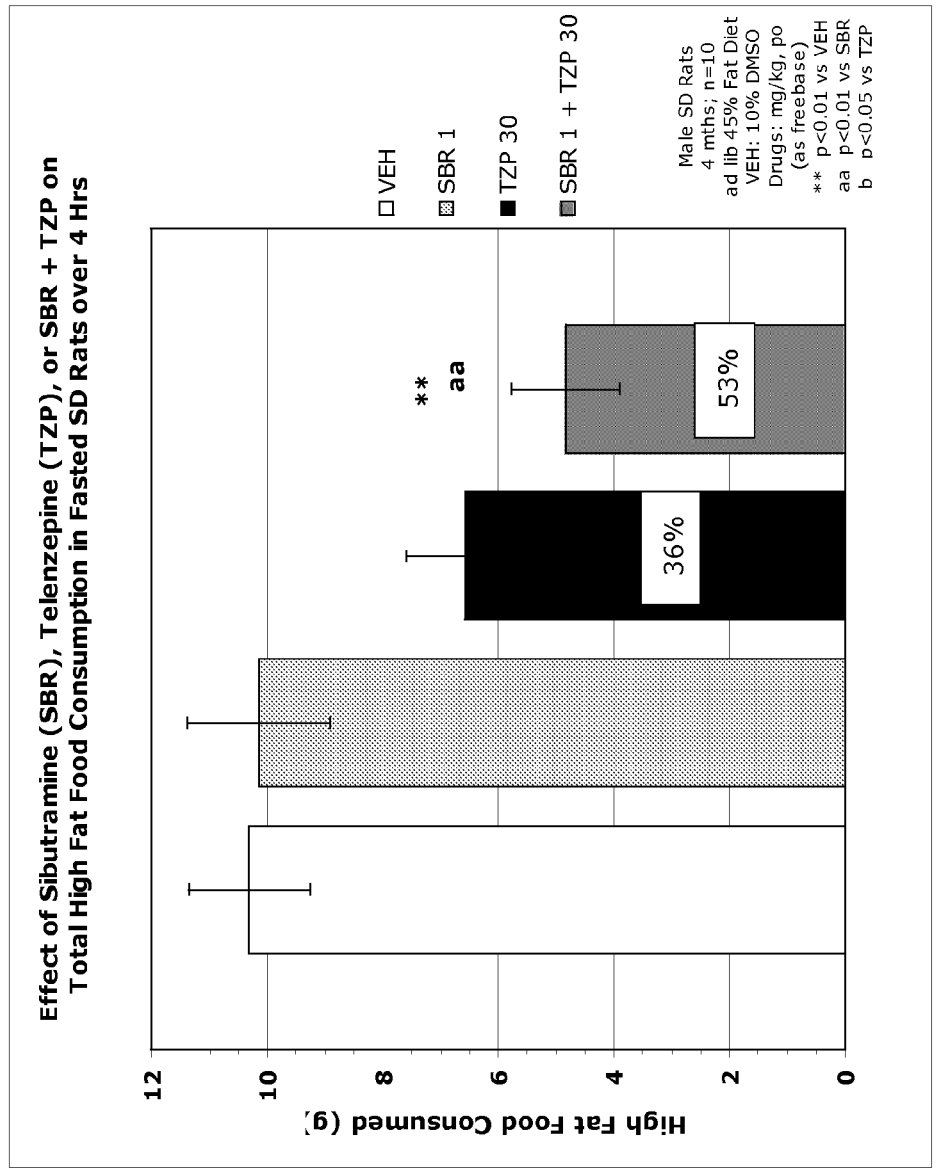
FIG. 4 illustrates the effect of telenzepine (TZP) alone, sibutramine (SBR) alone and combined telenzepine and sibutramine on total high fat food consumption in fasted rats over 4 hours. Four-month old male Sprague-Dawley rats (n=10 per group) were administered orally telenzepine alone (30 mg/kg), sibutramine alone (1.0 mg/kg), or co-administered telenzepine (30 mg/kg) and sibutramine (1.0 mg/kg), as described in the Examples below. All active agents were delivered in free base form. Control rats (VEH) were administered 10% DMSO. ** indicates p<0.01 vs. VEH. "aa" indicates p<0.01 vs. SBR.
Figure 5:
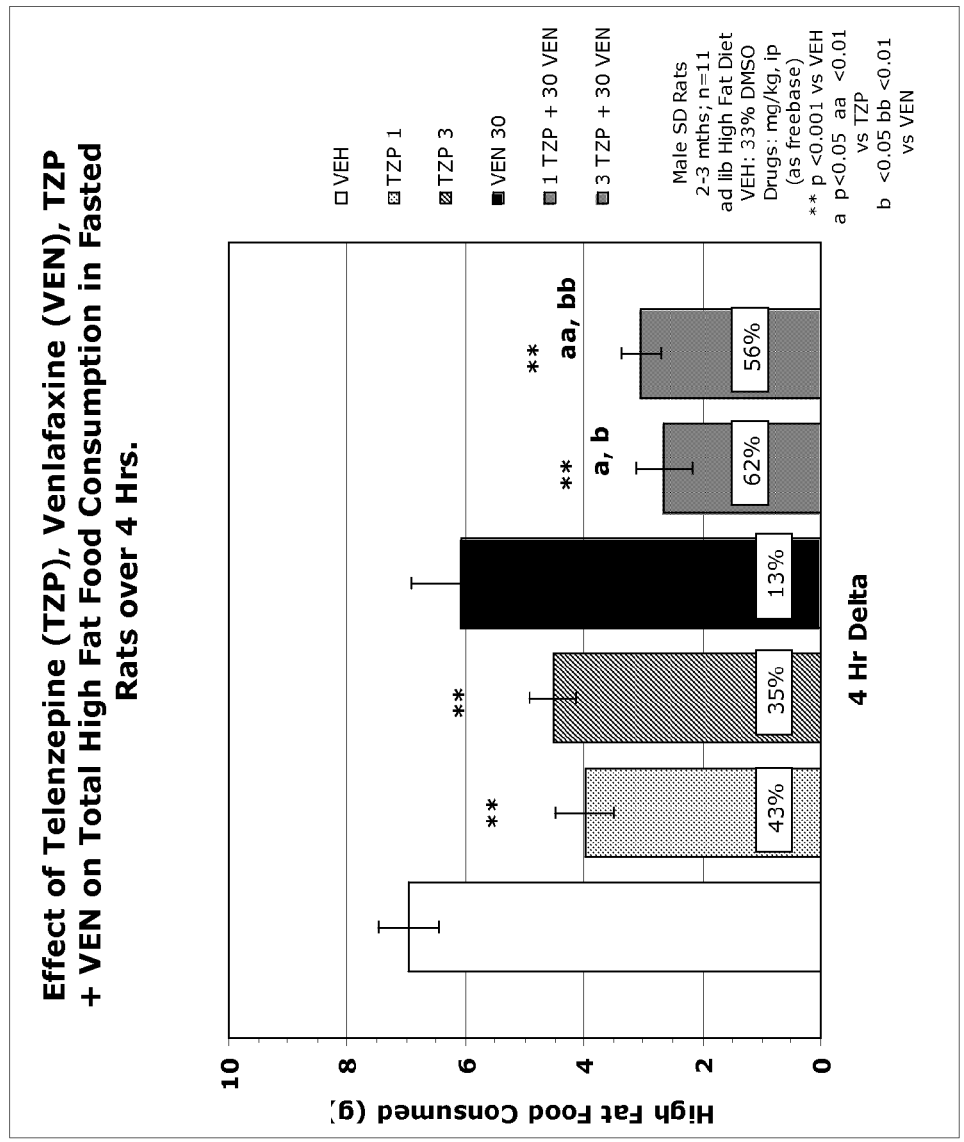
FIG. 5 illustrates the effect of telenzepine (TZP) alone, venlafaxine (VEN) alone and combined telenzepine and venlafaxine on total high fat food consumption in fasted rats over 4 hours. Two/Three-month old male Sprague-Dawley rats (n=11 per group) were administered intraperitoneally telenzepine alone (1 mg/kg or 3 mg/kg), venlafaxine alone (30 mg/kg), or co-administered telenzepine (1 mg/kg or 3 mg/kg) and venlafaxine (30 mg/kg), as described in the Examples below. All active agents were delivered in free base form. Control rats (VEH) were administered 33% DMSO. ** indicates p<0.001 vs. VEH. "a" indicates p<0.05 vs. TZP. "aa" indicates p<0.01 vs. TZP. "b" indicates p<0.05 vs. VEN. "bb" indicates p<0.01 vs. VEN.

As discussed above, earlier studies in rats and mice demonstrated that pirenzepine administered systemically failed to elicit any behavioral effects (see, Rogoz, Z., Skuza, G., Sowinska, H., *Pol. J. Pharmacol. Pharm.*, 1981, vol. 31, pp. 615-26), and that pirenzepine does not exhibit significant penetration of the blood-brain barrier in various species, including rodents and humans (see, Hammer, R., Koss, F. W., *Scand. J. GastroenteroL, Suppl.*, 1979, vol. 14, no. 57, pp. 1-6; Bymaster, F. P., et al., *J. Pharmacol. Exp. Ther.*, 1993, vol. 267, no. 1, pp. 16-24). Surprisingly, contrary to the published literature, the current invention demonstrates that $M_1R$-selective antagonists, including pirenzepine and telenzepine, can cross the blood-brain barrier in therapeutic amounts and therefore have useful pharmacological effects, including appetite suppression. Furthermore, contrary to previous understanding, the $M_1R$-selective antagonists can produce efficacious effects without administration at predetermined times in a 24 hour period.

The present invention also demonstrates that the use of $M_1R$-selective antagonists in combination with certain other therapeutic agents produces unexpected synergistic effects that are advantageous for pharmaceutical applications, including treating obesity and promoting weight loss.

The present invention provides an efficacious pharmacological treatment for achieving desired weight loss in an overweight or obese individual, and that effectuates continued weight loss and weight management over an extended period of time. Administration of a $M_1R$-selective antagonist unexpectedly provides for weight loss or reduced weight gain. Furthermore, co-administration of one or more $M_1R$-selective antagonists and one or more antidepressant agents other than a $M_1R$-selective antagonist unexpectedly provides for weight loss or reduced weight gain of a greater amount than is accomplished by administering any of these categories of drug alone, especially in view of the weight gain side-effects commonly associated with the long-term administration of antidepressants (see, for example, Masand and Gupta, *Ann. Clin. Psych.* 14:175 (2002); and Deshmukh and Franco, Cleve. Clin. J. Med. 70:614 (2003)). In some embodiments, the $M_1R$-selective antagonist can be co-administered with an anti-obesity agent.

2. Methods of Treating Obesity and/or Effectuating Weight Loss a. Conditions Subject to Treatment The present methods and compositions find use in the treatment of weight-related disorders. Exemplified general categories of disorders treatable by the present methods and compositions include, without limitation, obesity, retaining undesired or excessive weight, lack of satiation, among others.

The action of acetylcholine on muscarinic receptors in the central nervous system influences a diverse array of behaviors, including cognition, insight, vigilance, affect, sensorymotor gating and both reflexive and directed motility (Bymaster et al., Curr Drug Targets CNS Neurol Disord (2002) 1:163-181). Muscarinic receptors influence these functions not only through interactions with cholinergic neurons, but also through modulation of the activity of forebrain/midbrain dopaminergic, GABAergic and glutamatergic neurons. Neurolocalization and microdialysis studies have confirmed the influence muscarinic receptors and their agonists or antagonists have over these systems, with the directionality of modulation (excitation/inhibition) dependent on the specific receptor subtype. Specifically, local microinjection of the $M_1/M_4$ preferring antagonist, pirenzepine, results in decreased dopamine efflux in the striatum (Smolders et al., J Neurochem (1997) 68:1942-1948). Similarly, when directly injected into the midbrain, the $M_1/M_4$ receptor preferring antagonist, telenzepine, produces reduced GABA efflux (Smolders et al., 1997, supra). Likewise, non-subtype selective antagonists, such as scopolamine, produce elevated acetylcholine levels in the forebrain (Izurieta-Sanchez et al., Eur J Pharmacol (2000) 399:151-160).

With regard to disorders of dependence, including insatiability and compulsive overeating, mesolimbic dopamine circuits are thought to play important roles in the formation and perpetuation of addictive behavior (Berridge and Robinson, Brain Res Brain Res Rev (1998) 28:309-369; Crespo et al., J Neurosci (2006) 26:6004-6010; Di Chiara and Imperato, Proc Natl Acad Sci USA (1988) 85:5274-5278; Hernandez and Hoebel, Life Sci (1988) 42:1705-1712). Studies with rodents have shown that a specific structure in the striatum, the nucleus accumbens (NAc), is involved in the regulation of reward and aversion. The NAc lies in the medioventral striatum and can be further dissected into shell, core and rostral pole subterritories (Zahm and Brog, Neuroscience (1992) 50:751-767).

Rats will self-administer dopamine agonists into the NAc (Hoebel et al., Psychopharmacology (Berl) (1983) 81:158-163) and a large number of drugs that are known to provoke abuse and habituation in humans have been shown to increase extracellular dopamine levels in the NAc (Di Chiara and Imperato, 1988, supra; Hernandez and Hoebel, 1988, supra; Rada et al., Pharmacol Biochem Behav (1996) 53:809-816). Conversely, decreased extracellular dopamine in the nucleus accumbens has been observed to accompany aversion during morphine-induced and nicotine-induced withdrawal (Acquas and Di Chiara, (1992) J Neurochem 58:1620-1625; Diana et al., J Pharmacol Exp Ther (1995) 272:781-785; Pothos et al., Brain Res (1991) 566:348-350; Rada et al., Psychopharmacology (Berl) (2001) 157:105-110). The effects of dopamine appear to be mediated by receptor subtypes D1 and D2. Injection of dopamine D1 or D2 agonists into the NAc shell but not core, has been shown to reinstate drug-seeking behavior in rats that have been operantly conditioned to press levers for cocaine, but then have had the behavior extinguished by substituting saline for cocaine (Schmidt et al., Eur J Neurosci (2006) 23:219-228).

Within the NAc cholinergic and dopaminergic circuits appear to be pharmacologically opposed. Local intra-accumbal administration of either atropine (a nonspecific muscarinic antagonist) or mecamylamine (a nonspecific nicotinic antagonist) has been reported to block the acquisition of opiate reinforcement (Crespo et al., 2006, supra), whereas morphine decreases acetylcholine levels in the NAc (Fiserova et al., Psychopharmacology (Berl) (1999) 142:85-94; Rada et al., Neuropharmacology (1991) 30:1133-1136) and naloxone-induced opiate withdrawal increases acetylcholine levels (Fiserova et al., 1999, supra; Rada et al., 1991 supra; Rada et al., 1996, supra). Similar phenomena have been observed in conjunction with mecamylamine-induced withdrawal in nicotine-dependent rats (Rada et al., 2001, supra). In support of a broad general connection between elevated ACh and dysphoric states, ACh is released in the NAc by a conditioned aversive taste (Mark et al., Brain Res (1995) 688:184-188), aversive brain stimulation (Rada and Hoebel, Brain Res (2001) 888:60-65), and withdrawal from diazepam (Rada and Hoebel, Eur J Pharmacol (2005) 508:131-138), alcohol (Rada et al., Pharmacol Biochem Behav (2004) 79:599-605) or sugar (Colantuoni et al., Obes Res (2002) 10, 478-488). Attenuation of cholinergic transmission is thus a therapeutically attractive approach to the treatment of disorders of addiction and habituation. Such disorders need not be purely pharmacologic as the findings with sucrose withdrawal exemplify.

Accordingly, neuropsychiatric applications for compounds that possess the ability to preferentially modulate $M_1$ muscarinic receptors are widespread. Therefore, the present methods find use in treating a variety of conditions, including those resulting from impaired: i) cognitive processing, ii) affective processing, and/or iii) appetitive motivation. Conditions within these categories include impulse control disorders and appetite disorders that result in obesity or retention of excessive and/or undesirable body fat.

Accordingly, the present methods and compositions find use in treating obesity, suppressing appetite, promoting desirable weight loss, facilitating maintenance of a desired weight, and preventing or decreasing undesirable weight gain.

b. Pharmacological Agents

The pharmacological agents used in the present methods and compositions include the one or more active agents, described in detail below, in any pharmaceutically acceptable form, including any pharmaceutically acceptable salts, prodrugs, racemic mixtures, conformational and/or optical isomers, crystalline polymorphs and isotopic variants of the one or more pharmacological agents.

i. Selective Muscarinic Receptor $M_1$ Antagonists

The present methods treat obesity and promote weight loss and appetite suppression by administering to an individual in need thereof a therapeutic amount of one or more selective muscarinic receptor $M_1$ antagonists. Muscarinic antagonists are generally reviewed in Chapter 7 of Goodman and Gilman's The Pharmacological Basis of Therapeutics, supra, hereby incorporated herein by reference. Exemplified selective muscarinic receptor $M_1$ antagonists include pirenzepine and telenzepine, the structures of which are shown below.

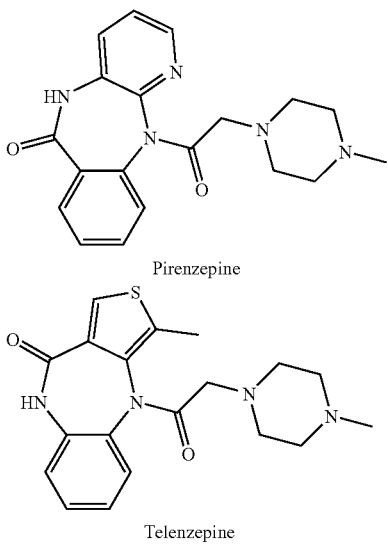

Pirenzepine

Telenzepine

Pirenzepine (5,11-Dihydro-11-[(4-methyl-1-piperazinyl)acetyl]-6H-pyrido[2,3-b][1,4]benzodiazepin-6-one) is manufactured and sold as pirenzepine dihydrochloride by several pharmaceutical companies, including Azupharma (Stuttgart, Germany), Boehringer Ingelheim (Ingelheim, Germany; sold as Gastrozepin®), Dolorgiet (Bonn, Germany). Pirenzepine can be administered in doses from about 50 mg/day to about 200 mg/day, for example, about 100-150 mg/day, or 50, 100, 150, or 200 mg/day. Alternatively, pirenzepine can be administered in doses of about 0.1 mg/kg/day to about 10 mg/kg/day, usually from about 0.7 mg/kg/day to about 5 mg/kg/day. Analogs of pirenzepine also find use in carrying out the present methods. Chemical analogs of pirenzepine are disclosed, for example, in U.S. Pat. Nos. 3,660,380; 3,743,734; and 5,324,832, the disclosures of each of which are hereby incorporated herein by reference in their entirety for all purposes. Further dosage regimens for pirenzepine are disclosed, for example, in U.S. Pat. No. 5,668,155.

Telenzepine (4,9-Dihydro-3-methyl-4-[(4-methyl-1-piperazinyl)acetyl]-10H-thieno[3,4-b][1,5]benzodiazepin-10-one) is commercially available from, for example, Tocris Bioscience (Ellisville, Mo.) and Sigma-Aldrich, Inc. (St. Louis, Mo.) as telenzepine dihydrochloride. Further, the synthesis of telenzepine is disclosed in U.S. Pat. No. 4,381,301, hereby incorporated herein by reference. Telenzepine can be administered in doses from about 0.5 mg per day to about 10 mg per day, for example, about 1-5 mg/day, or 0.5, 1, 2, 3, 4, 5, 6, 7, 8, 9 or 10 mg/day. According to U.S. Pat. No. 4,381,301, telenzepine can be administered orally in a daily dose of from about 0.01 to about 5, preferably from 0.05 to 2.5 and, in particular, from 0.1 to 1.5, mg/kg of body weight, generally in the form of several, preferably 1 to 3, individual administrations in order to achieve the desired results. An individual administration contains the active compound or compounds in an amount of from about 0.01 to about 2.5, preferably from 0.01 to 1.5 and, in particular, from 0.05 to 0.5, mg/kg of body weight. Similar dosages are used for parenteral, for example intravenous, treatment. Analogs of telenzepine also find use in carrying out the present methods. Chemical analogs and enantiomers of telenzepine are disclosed, for example, in U.S. Pat. Nos. 3,953,430; 4,168,269; 4,172,831; 4,381,301; 5,140,025 and 5,324,832, the disclosures of each of which are hereby incorporated herein by reference in their entirety for all purposes.

In some embodiments a racemic preparation of telenzepine containing a mixture of (+) and (−) enantiomers is administered. In some embodiments, the (+) or (−) enantiomer of telenzepine is administered. Telenzepine exists in two chirally distinct states separated by an activation barrier of 35.5 kcal/mol (Eveleigh et al., *Mol Pharmacol* (1989) 35:477-483; and Schudt et al., *Eur J Pharmacol* (1989) 165: 87-96). The (+) form of telenzepine has potent antimuscarinic activity whereas the (−) form is considerably less active. The selectivity of telenzepine appears to vary at different anatomic sites with the (+) form more effective on cortical receptors by a factor of 400 compared to the (−) isomer; on cardiac receptors the selectivity is less and the (+) form is more potent than the (−) form by a factor of 50 (Eveleigh et al., supra). The two forms interconvert slowly and with a half time of approximately 200 hours at 90 degrees (Eveleigh et al., supra). Multiple studies have affirmed that the two forms have distinct activities (Eltze, *Eur J Pharmacol* (1990) 180:161-168; Eveleigh et al., supra; Feifel et al., *Eur J Pharmacol* (1991) 195:115-123; Kilian et al., *Agents Actions Suppl* 34:131-147; Schudt et al., supra).

ii. Anti-Depressants

Antidepressant agents that are not $M_1R$-selective antagonists for use in the present invention are not limited by their mechanism of action and any class of antidepressant is applicable. For instance, tricyclic antidepressants (TCAs) and analogs thereof, serotonin reuptake inhibitors, monoamine oxidase inhibitors (MAOIs), serotonin agonists and prodrugs thereof, norepinephrine reuptake inhibitors, dopamine reuptake inhibitors, and serotonin reuptake accelerators can all be administered in combination with one or more $M_1R$-selective antagonists. Serotonin reuptake inhibitors include both selective serotonin reuptake inhibitors (SSRIs) and serotonin-norepinephrine reuptake inhibitors (SNRIs). Norepinephrine reuptake inhibitors include both the specific norepinephrine reuptake inhibitors as well as the mixed norepinephrine-dopamine reuptake inhibitors (NDRIs). Serotonin-norepinephrine-dopamine, or "triple reuptake inhibitors" also find use in the present invention. Other categories of antidepressant can also be used, for example, the tetracyclic antidepressants maprotiline or mianserin, or the agents trazodone, nefazodone, or buspirone; corticotropin releasing factor receptor 1 (CRF1) antagonists, and compounds discovered to have activity in the setting of psychosis or bipolar disorder, including amoxapine, clozapine, risperidone, olanzapine, quetiapine and aripiprazole.

Tricyclic antidepressants for use in the present invention include amineptine, amitriptyline, clomipramine, desipramine, doxepin, dothiepin, imipramine, nortriptyline, protriptyline, trimipramine, amoxapine and the muscle relaxant cyclobenzaprine. Other unlisted tricyclic antidepressants and analogs thereof can also be used.

In one embodiment, an effective amount of one or more $M_1R$-selective antagonists is co-administered with an effective amount of a selective serotonin reuptake inhibitor. Exemplary selective serotonin reuptake inhibitors include citalopram, escitalopram, fluoxetine (racemic or an optical isomer), fluvoxamine, paroxetine and sertraline (and its S-enantiomer, Zoloft®), although SSRIs not listed are applicable. In one embodiment, citalopram (or escitalopram) is co-administered with one or more $M_1R$-selective antagonists. In one embodiment, an effective amount of fluoxetine (racemic or an optical isomer) is co-administered. In one embodiment, an effective amount of fluvoxamine is co-administered. In one embodiment, an effective amount of sertraline (or its S-enantiomer, Zoloft®) is co-administered. In one embodiment, an effective amount of paroxetine is co-administered. In one embodiment, an effective amount of duloxetine is co-administered.

In one embodiment, an effective amount of one or more serotonin-norepinephrine reuptake inhibitors are co-administered with one or more $M_1R$-selective antagonist. Exemplary serotonin-norepinephrine reuptake inhibitors include milnacipran, mirtazapine, venlafaxine (racemic or an optical isomer), duloxetine, (−)1-(1-dimethylaminomethyl-5-methoxybenzo-cyclobutan-1-yl)cyclohexanol (S33005), DVS-233 (desvenlafaxine), DVS-233 SR and sibutramine, although SNRIs not listed are also of use. Although the mechanism of action of mirtazapine may differ from that of other SNRIs, owing to its apparent dual serotonergic and noradrenergic action, it is considered herein as a member of the SNRI class of antidepressants. In one embodiment, an effective amount of venlafaxine (racemic or an optical isomer) is co-administered. In one embodiment, an effective amount of desvenlafaxine is co-administered. In one embodiment, an effective amount of sibutramine is co-administered. In one embodiment, an effective amount of duloxetine is co-administered. In one embodiment, an effective amount of milnacipran is co-administered. In one embodiment, an effective amount of mirtazapine is co-administered.

In other embodiments, an effective amount of one or more selective norepinephrine reuptake inhibitors is co-administered with one or more $M_1R$-selective antagonists. Exemplary selective norepinephrine reuptake inhibitors include reboxetine and atomoxetine.

In one embodiment, an effective amount of one or more norepinephrine-dopamine reuptake inhibitors are co-administered with one or more $M_1R$-selective antagonists. Exemplary norepinephrine-dopamine reuptake inhibitors include amineptine, modafinil, GW353162 and bupropion. In the case of bupropion, metabolites are thought to be responsible for the noradrenergic reuptake blockade. In one embodiment, an effective amount of bupropion is co-administered.

In one embodiment, an effective amount of one or more triple (serotonin-norepinephrine-dopamine) reuptake inhibitors are co-administered with one or more $M_1R$-selective antagonist. Exemplary triple reuptake inhibitors include indatraline, SEP-225289, DOV 216,303 and (+)-1-(3,4-dichlorophenyl)-3-azabicyclo-[3.1.0]hexane hydrochloride (DOV 21,947).

Monoamine oxidase inhibitors for use in the present invention include befloxatone, brofaromine, deprenyl, isocarboxazid, moclobemide, pargyline, phenelzine, selegiline and tranylcypromine, together with their sustained delivery and transdermal delivery forms.

Antidepressants that can be co-administered with an $M_1R$-selective antagonist include maprotiline, tianeptine, nefazodone and trazodone.

Appropriate dosages for antidepressants will depend on the chosen route of administration and formulation of the composition, among other factors. For instance, tricyclic antidepressants are administered at a dose of about 25 to about 600 mg/day, and usually at a dose of about 75 to about 300 mg/day.

Serotonin-reuptake inhibitors are administered at a dose of about 5 to about 400 mg/day, and usually administered at about 20 to about 250 mg/day. In particular, in practicing the present methods, venlafaxine (racemic or an optical isomer) can be administered at about 9 mg to about 225 mg per dose, and is usually administered at about 37.5 mg, 75 mg, 150 mg or 225 mg per dose. Venlafaxine is typically administered at about 25-550 mg/day and usually at about 37.5-375 mg/day, more typically about 75-225 mg/day, and most typically at about 37.5, 75, 150, 225, or 300 mg/day. As appropriate for an individual patient, daily venlafaxine dosages can be divided and administered one time, two times, three times, four or more times a day. Desvenlafaxine can be administered at a dose of about 50-600 mg/day, for example, about 50, 100, 200, 400 or 600 mg/day. Sertraline (or its S-enantiomer, Zoloft®) can be administered in doses ranging from about 50-200 mg/day, usually about 100-150 mg/day. Fluoxetine (racemic or an optical isomer) can be administered in doses ranging from about 5-50 mg/day, usually about 20-40 mg/day. Fluvoxamine can be administered in doses ranging from about 50-300 mg/day, usually about 100-200 mg/day. Paroxetine can be administered in doses ranging from about 10-50 mg/day, usually about 20-40 mg/day.

In carrying out the present methods, citalopram (or escitalopram) can be administered at about 5-60 mg/day, and preferably at about 10, 20 or 30 mg/day. Usually, citalopram is administered once a day, for instance in the morning or in the evening. However, some patients are given dosages of citalopram two or more times a day. Mirtazapine can be administered at a dose of about 5-100 mg/day, for example, about 7.5, 15, 30, 45 or 90 mg/day. Milnacipran can be administered at a dose of about 25-200 mg/day, for example, about 25, 50, 100, 150 or 200 mg/day.

Atypical antidepressants, including bupropion, nefazodone and trazodone are administered at a dose of about 50-600 mg/day, and usually at about 150-400 mg/day. Bupropion can be administered at a dose of about 25-300 mg/day, for example, about 25, 50, 100, 150, 200, 300 mg/day. Monoamine oxidase inhibitors are typically administered at a dose of about 5-90 mg/day, and usually at about 10-60 mg/day.

iii. Anti-Obesity Agents

The present invention also contemplates administering an effective amount of one or more $M_1R$-selective antagonists in combination with one or more anti-obesity agents. In addition, the present invention contemplates administering an effective amount of a combination of one or more $M_1R$-selective antagonists and one or more antidepressants optionally in further combination with one or more anti-obesity agents. Examples of anti-obesity agents suitable for use (i) in combination with one or more $M_1R$-selective antagonists, or (ii) in further combination with a combination of $M_1R$-selective antagonists and antidepressants include anorexiants, dopamine agonists, $H_3$-histamine antagonists, 5-HT2c receptor agonists, beta-3 adrenergic receptor agonists, cholecystokinin agonists, anti-epileptic agents, leptin, leptin analogs and leptin receptor agonists, neuropeptide Y (NPY) receptor antagonists and modulators, peptide-YY (PYY) receptor agonists, ciliary neurotrophic factor, thyroid hormone receptor-beta agonists, cannabinoid CB1 receptor antagonists, melanin-concentrating hormone receptor antagonists, pancreatic and gastric lipase inhibitors, melanocortin-4 receptor agonists, and combinations thereof.

Exemplified anorexiants include amphetamine, methamphetamine, dextroamphetamine, phentermine, benzphetamine, phendimetrazine, phenmetrazine, diethylpropion, mazindol, fenfluramine, dexfenfluramine, phenylpropanolamine, ephedra and the like. The anorexiant can be a sympathomimetic amine.

Exemplified dopamine agonists include ER-230, doprexin, bromocriptine mesylate and the like.

Exemplified $H_3$-histamine antagonists include impentamine, thioperamide, ciproxifan, clobenpropit, GT-2331, GT-2394, A-331440 and the like.

Exemplified 5-HT2c receptor agonists include 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson B M, J. Med. Chem. 2006, 49:4023-4034).

Exemplified beta-3 adrenergic receptor agonists include L-796568, CGP 12177, BRL-28410, SR-58611A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like.

Exemplified cholecystokinin agonists include SR-146131, SSR-125180, BP-3.200, A-71623, A-71378, FPL-15849, GI-248573, GW-7178, GI-181771, GW-7854, GW-5823, and the like.

Exemplified pancreatic and gastric lipase inhibitors include orlistat, cetilistat (ATL-962) and the like.

Exemplified anti-epileptic agents include topiramate, zonisamide and the like.

Other anti-obesity agents of use include leptin, leptin analogs and leptin receptor agonists (including LY-355101 and the like), neuropeptide Y (NPY) receptor antagonists and modulators (including SR-120819-A, PD-160170, NGD-95-1, BIBP-3226, 1229-U-91, CGP-71683, BIBO-3304, CP-671906-01, J-115814 and the like), peptide-YY (PYY) receptor agonists (including PYY(3-36) and the like), ciliary neurotrophic factor (including Axokine and the like), thyroid hormone receptor-beta agonists (including KB-141, GC-1, GC-24, GB98/284425 and the like), cannabinoid CB1 receptor antagonists (including rimonabant, SR147778, SLV 319 and the like (see, e.g., Antel J et al., *J. Med. Chem.* 2006, 49:4008-4016)), melanin-concentrating hormone receptor antagonists (including GlaxoSmithKline 803430X, GlaxoSmithKline 856464, SNAP-7941, T-226296 and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., *J. Med. Chem.* 2006, 49:4035-4043)) and combinations thereof.

iv. Combinations of Pharmacological Agents

In some embodiments, the one or more $M_1R$-selective antagonists are co-administered or co-formulated with one or more antidepressants that are not a $M_1R$-selective antagonist. In some embodiments, the one or more $M_1R$-selective antagonists are co-administered or co-formulated with one or more anti-obesity agents. In some embodiments, the one or more $M_1R$-selective antagonists are co-administered or co-formulated with one or more antidepressants that are not a $M_1R$-selective antagonist and one or more anti-obesity agents. The $M_1R$-selective antagonists, antidepressants and anti-obesity agents are as described above.

v. Isomers

All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers of the therapeutic agents are within the scope of the present invention.

vi. Isotopes

The present invention also includes isotopically-labeled variants of the therapeutic agents, wherein one or more atoms are replaced by one or more atoms having specific atomic mass or mass numbers. Isotopically-labeled variants of the therapeutic agents and prodrugs thereof, as well as isotopically-labeled, pharmaceutically acceptable salts of the therapeutic agents and prodrugs thereof, are within the scope of the present invention. In certain circumstances substitution with heavier isotopes, such as deuterium ($^2H$), can provide increased metabolic stability, which offers therapeutic advantages such as increased in vivo half-life or reduced dosage requirements. Isotopically-labeled variants of the therapeutic agents of this invention and prodrugs thereof can generally be prepared according to methods known to those skilled in the art by substituting an isotopically-labeled reagent for a non-isotopically labeled reagent.

c. Administration i. Duration of Administration

Usually, the one or more $M_1R$-selective antagonists are administered to the individual over an extended period of time. The methods can be carried out for at least 20 days, in some embodiments for at least 40, 60, 80 or 100 days, and in some embodiments for at least 150, 200, 250, 300, 350 days, 1 year or longer. Certain individuals receive the present treatment methods for longer than a year, for example, at least 400, 450, 500, 550, 600, 650, 700, 800, 900, 1000 days. However, individuals can be successfully treated with the present methods for 2 years, 3 years, 4 years or longer.

Usually, subjects treated according to the present invention can lose at least about 5 to 15 pounds after about 50 to 70 days of treatment, at least about 10 to 25 pounds after about 90 to 150 days of treatment, and at least about 15 to 45 pounds after about 200 to 400 days of treatment. Typically, individuals treated according to the present methods can lose at least about 5%, and more usually at least about 10%, 15% or 20% of their baseline body weight, and stably maintain this desired weight loss by carrying out a treatment regimen for 100, 150, 200, 250, 300, 350, 400, 450, 500, 550, 600, 700, 800, 900, 1000 days or more. Importantly, administering an effective amount of one or more antidepressants over an extended period of time facilitates a stable weight status and the prevention of undesired weight gain throughout the extended time period of treatment. The combination treatment of the present invention is particularly appropriate for obese and overweight individuals, but can also be administered to any individual who desires to lose weight, maintain a stable weight or prevent unwanted weight gain.

ii. Scheduling

Generally, in practicing the present methods, effective amounts of one or more $M_1R$-selective antagonists are administered alone or co-administered with one or more antidepressants other than a $M_1R$-selective antagonist. In some embodiments, effective amounts of one or more $M_1R$-selective antagonists are co-administered with one or more anti-obesity agents. In some embodiments, effective amounts of one or more $M_1R$-selective antagonists are co-administered with one or more antidepressants other than a $M_1R$-selective antagonist and one or more anti-obesity agents. Co-administered pharmacological agents can be administered together or separately, simultaneously or at different times. When administered, the $M_1R$-selective antagonists, antidepressants and anti-obesity agents independently can be administered once, twice, three, four times daily or more or less often, as needed. Preferably, the administered pharmacological agents are administered once daily. Preferably, the administered active agents are administered at the same time or times, for instance as an admixture. One or more of the pharmacological agents can be administered in a sustained-release formulation.

For certain patients, the methods are carried out concurrently administering the one or more $M_1R$-selective antagonists and then the one or more antidepressants and/or one or more anti-obesity agents from the initiation of treatment. For certain patients, the methods are carried out by first administering the one or more $M_1R$-selective antagonists, and then subsequently co-administering the one or more antidepressants and/or one or more anti-obesity agents. The patient initially can be given the one or more $M_1R$-selective antagonists alone for as long as 3 days, 5 days, 7 days, 10 days, 14 days, 20 days, or 30 days before commencing administration of one or more antidepressants and/or one or more anti-obesity agents.

When administered for the purpose of facilitating weight loss or suppressing appetite, the one or more $M_1R$-selective antagonists, alone or in combination, can be administered prophylactically to prevent undesirable weight gain or maintain a stable weight, or therapeutically to achieve a desired weight loss and maintain such weight loss for a sustained period of time.

iii. Routes of Administration

As such, administration of one or more $M_1R$-selective antagonists, alone or in combination with one or more antidepressants and/or one or more anti-obesity agents, can be achieved in various ways, including oral, buccal, parenteral, including intravenous, intradermal, subcutaneous, intramuscular, transdermal, transmucosal, intranasal, etc., administration. The one or more $M_1R$-selective antagonists can be administered by the same or different route of administration when co-administered with one or more antidepressants and/or one or more anti-obesity agents.

In some embodiments, one or more $M_1R$-selective antagonists, alone or in combination, can be administered in a local rather than systemic manner, for example, in a depot or sustained release formulation.

iv. Methods of Determining Appropriate Dosages

Administered dosages for $M_1R$-selective antagonists, antidepressants and anti-obesity agents are in accordance with dosages and scheduling regimens practiced by those of skill in the art. General guidance for appropriate dosages of all pharmacological agents used in the present methods is provided in *Goodman and Gilman's The Pharmacological Basis of Therapeutics*, 11th Edition, 2006, supra, and in a Physicians' Desk Reference (PDR), for example, in the $59^{th}$ (2005) or $60^{th}$ (2006) Eds., Thomson PDR, each of which is hereby incorporated herein by reference. Published dosages for $M_1R$-selective antagonists are for indications distinct from treatments to treat obesity or to promote weight loss or inhibit weight gain. In the compositions and methods of the present invention, efficacious dosages of $M_1R$-selective antagonists, antidepressants and anti-obesity agents for practicing the present invention can be equal to or less than (e.g., about 25, 50, 75 or 100%) the dosages published for other indications.

The appropriate dosage of $M_1R$-selective antagonists, antidepressants and anti-obesity agents will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

Determination of an effective amount is well within the capability of those skilled in the art, especially in light of the detailed disclosure provided herein. Generally, an efficacious or effective amount of a combination of one or more $M_1R$-selective antagonists and one or more antidepressants and/or one or more anti-obesity agents is determined by first administering a low dose or small amount of an $M_1R$-selective antagonist alone, and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics*, 11th Edition, 2006, supra; in a Physicians' Desk Reference (PDR), supra; in *Remington: The Science and Practice of pharmacy*, $21^{st}$ Ed., 2006, supra; and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

3. Pharmaceutical Compositions

The present invention further provides pharmaceutical compositions comprising a mixture of a therapeutically effective amount of one or more $M_1R$-selective antagonists and one or more antidepressants and/or one or more anti-obesity agents. In some embodiments, the $M_1R$-selective antagonists are selected from the group consisting of telenzepine, pirenzepine and mixtures thereof.

In certain embodiments, the pharmaceutical compositions comprise one or more antidepressants that are a selective serotonin reuptake inhibitor (SSRI), a serotonin-norepinephrine reuptake inhibitor (SNRI), a norepinephrine reuptake inhibitor, a dopamine reuptake inhibitor, a norepinephrine-dopamine reuptake inhibitor (NDRI), a serotonin-norepinephrine-dopamine reuptake inhibitor, a serotonin reuptake accelerator, a serotonin agonist and prodrugs thereof. In one embodiment, the pharmaceutical composition comprises one or more antidepressants selected from the group consisting of venlafaxine (racemic or an optical isomer), duloxetine, fluoxetine (racemic or an optical isomer), citalopram, escitalopram, fluvoxamine, paroxetine, S33005, DVS-233 (desvenlafaxine), DVS-233 SR, bupropion, GW353162, sibutramine, atomoxetine and sertraline (or its S-enantiomer, Zoloft®).

In one embodiment, the pharmaceutical composition comprises therapeutically effective amounts of telenzepine or pirenzepine and an SSRI. In one embodiment, the pharmaceutical composition comprises therapeutically effective amounts of telenzepine or pirenzepine and citalopram (or escitalopram). In one embodiment, the pharmaceutical composition comprises therapeutically effective amounts of telenzepine or pirenzepine and sertraline (or its S-enantiomer, Zoloft®). In one embodiment, the pharmaceutical composition comprises therapeutically effective amounts of telenzepine or pirenzepine and fluoxetine (racemic or an optical isomer). In one embodiment, the pharmaceutical composition comprises therapeutically effective amounts of telenzepine or pirenzepine and fluvoxamine. In one embodiment, the pharmaceutical composition comprises therapeutically effective amounts of telenzepine or pirenzepine and paroxetine.

In one embodiment, the pharmaceutical composition comprises therapeutically effective amounts of telenzepine or pirenzepine and an SNRI. In one embodiment, the pharmaceutical composition comprises therapeutically effective amounts of telenzepine or pirenzepine and venlafaxine (racemic or an optical isomer). In one embodiment, the pharmaceutical composition comprises therapeutically effective amounts of telenzepine or pirenzepine and desvenlafaxine. In one embodiment, the pharmaceutical composition comprises therapeutically effective amounts of telenzepine or pirenzepine and duloxetine. In one embodiment, the pharmaceutical composition comprises therapeutically effective amounts of telenzepine or pirenzepine and milnacipran. In one embodiment, the pharmaceutical composition comprises therapeutically effective amounts of telenzepine or pirenzepine and mirtazapine.

In one embodiment, the pharmaceutical composition comprises therapeutically effective amounts of telenzepine or pirenzepine and bupropion.

A combination of one or more $M_1R$-selective antagonists and one or more antidepressants and/or one or more anti-obesity agents can be administered to a subject, e.g., a human patient, a domestic animal such as a cat or a dog, independently or together in the form of their pharmaceutically acceptable salts, or in the form of a pharmaceutical composition where the compounds are mixed with suitable carriers or excipient(s) in a therapeutically effective amount, e.g., at doses effective to effect desired weight loss or maintenance or prevent undesired weight gain.

A combination of one or more $M_1R$-selective antagonists and one or more antidepressants and/or one or more anti-obesity agents of this invention can be incorporated into a variety of formulations for therapeutic administration. More particularly, a combination of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Suitable formulations for use in the present invention are found in, for example, in *Remington: The Science and Practice of Pharmacy,* 21$^{st}$ Ed., 2006, supra; *Martindale: The Complete Drug Reference*, Sweetman, 2005, London: Pharmaceutical Press.; Niazi, *Handbook of Pharmaceutical Manufacturing Formulations,* 2004, CRC Press; and Gibson, *Pharmaceutical Preformulation and Formulation: A Practical Guide from Candidate Drug Selection to Commercial Dosage Form,* 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one embodiment, a combination of one or more $M_1R$-selective antagonists and one or more antidepressants and/or one or more anti-obesity agents is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Peamchob, et al. Drug Dev. Ind. Pharm. 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a combination of one or more $M_1R$-selective antagonists and one or more antidepressants and/or one or more anti-obesity agents of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a combination of one or more $M_1R$-selective antagonists and one or more antidepressants and/or one or more anti-obesity agents can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, a combination of one or more $M_1R$-selective antagonists and one or more antidepressants and/or one or more anti-obesity agents can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a combination of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in a conventional manner.

In addition to the formulations described previously, a combination of one or more $M_1R$-selective antagonists and one or more antidepressants and/or one or more anti-obesity agents of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

4. Kits

The pharmaceutical compositions of the present invention can be provided in a kit. In certain embodiments, a kit of the present invention comprises one or more $M_1R$-selective antagonists and one or more antidepressants and/or one or more anti-obesity agents in separate formulations. In certain embodiments, the kits comprise one or more $M_1R$-selective antagonists and one or more antidepressants and/or one or more anti-obesity agents within the same formulation. In certain embodiments, the kits provide the one or more $M_1R$-selective antagonists and one or more antidepressants and/or one or more anti-obesity agents independently in uniform dosage formulations throughout the course of treatment. In certain embodiments, the kits provide the one or more $M_1R$-selective antagonists and one or more antidepressants and/or one or more anti-obesity agents independently in graduated dosages over the course of treatment, either increasing or decreasing, but usually increasing to an efficacious dosage level, according to the requirements of an individual.

In one embodiment, the kits comprise one or more pharmaceutical compositions comprising one or more $M_1R$-selective antagonists selected from the group consisting of telenzepine and pirenzepine.

In certain embodiments, the kits comprise one or more antidepressants selected from the group consisting of a selective serotonin reuptake inhibitor (SSRI), a serotonin-norepinephrine reuptake inhibitor (SNRI), a norepinephrine reuptake inhibitor, a dopamine reuptake inhibitor, a norepinephrine-dopamine reuptake inhibitor (NDRI), a serotonin-norepinephrine-dopamine reuptake inhibitor, and mixtures thereof. In one embodiment, the kits comprise one or more pharmaceutical compositions comprising one or more antidepressants selected from the group consisting of venlafaxine (racemic or an optical isomer), fluoxetine (racemic or an optical isomer), duloxetine, paroxetine, citalopram, escitalopram, fluvoxamine, S33005, DVS-233 (desvenlafaxine), DVS-233 SR, bupropion, GW353162, sibutramine, atomoxetine and sertraline (or its S-enantiomer, Zoloft®).

In one embodiment, the kit comprises therapeutically effective amounts of telenzepine or pirenzepine and an SSRI. In one embodiment, the kit comprises therapeutically effective amounts of telenzepine or pirenzepine and citalopram (or escitalopram). In one embodiment, the kit comprises therapeutically effective amounts of telenzepine or pirenzepine and sertraline (or its S-enantiomer, Zoloft®). In one embodiment, the kit comprises therapeutically effective amounts of telenzepine or pirenzepine and fluoxetine (racemic or an optical isomer). In one embodiment, the kit comprises therapeutically effective amounts of telenzepine or pirenzepine and fluvoxamine. In one embodiment, the kit comprises therapeutically effective amounts of telenzepine or pirenzepine and paroxetine.

In one embodiment, the kit comprises therapeutically effective amounts of telenzepine or pirenzepine and an SNRI. In one embodiment, the kit comprises therapeutically effective amounts of telenzepine or pirenzepine and venlafaxine (racemic or an optical isomer). In one embodiment, the kit comprises therapeutically effective amounts of telenzepine or pirenzepine and desvenlafaxine. In one embodiment, the kit comprises therapeutically effective amounts of telenzepine or pirenzepine and duloxetine. In one embodiment, the kit comprises therapeutically effective amounts of telenzepine or pirenzepine and milnacipran. In one embodiment, the kit comprises therapeutically effective amounts of telenzepine or pirenzepine and mirtazapine.

In one embodiment, the kit comprises therapeutically effective amounts of telenzepine or pirenzepine and bupropion.

In certain embodiments, the kits comprise one or more anti-obesity agents selected from the group consisting of anorexiants, dopamine agonists, $H_3$-histamine antagonists, 5-HT2c receptor agonists, beta-3 adrenergic receptor agonists, cholecystokinin agonists, anti-epileptic agents, leptin, leptin analogs and leptin receptor agonists, neuropeptide Y (NPY) receptor antagonists and modulators, peptide-YY (PYY) receptor agonists, ciliary neurotrophic factor, thyroid hormone receptor-beta agonists, cannabinoid CB1 receptor antagonists, melanin-concentrating hormone receptor antagonists, pancreatic and gastric lipase inhibitors, melanocortin-4 receptor agonists.

In one embodiment, the kit comprises therapeutically effective amounts of telenzepine or pirenzepine and phentermine.

EXAMPLES

The following examples are offered to illustrate, but not to limit the claimed invention.

Example 1

Appetite Suppression: Three-month-old (300-350 grams) male, Sprague-Dawley rats (individually housed) were used to assess compounds for their appetite suppressant effects. Rats were acclimatized to a "high fat" food diet (BioServ Diet #F3282 or Research Diets #12451) for two weeks prior to testing (access to food and water ad libitum). One day prior to the experiment (at 5:00 PM), food was removed from the cages in order to motivate feeding when the food was returned the following morning (water remained available throughout the experiment). Prior to presentation of the food, rats (n=8-10/dose group) were dosed intraperitoneally (ip) or orally (po) with the compound under investigation, returned to their home cage and immediately given a pre-weighed amount of food. Four hours after administration, the food was removed from the cage, weighed, recorded (4-Hour Consumption) and returned to the rat until the following morning. Twenty-four hours after administration, the remaining food was again weighed and recorded (24-Hour Consumption). Cumulative consumption (expressed in grams) was calculated for both the four and the twenty-four hour intervals. In this assay, vehicle-treated rats typically consume approximately 8 grams over the four-hour interval and approximately 25 grams over the twenty-four-hour interval.

Treatment effects are presented in Table 1 and FIGS. 1-5 (4-Hour Consumption) and Table 2 and FIGS. 6-10 (24-Hour Consumption). The effects are given as both Raw Consumption (in grams ±SEM [1 standard error of the mean]) and as % Reduction in 4-Hour or 24-Hour Consumption=[1-(Consumption following Drug Treatment/Consumption following Vehicle Treatment)]×100%. Similar superscripts in the Dose column of Tables 1 and 2 denote values derived from the same experiment (to facilitate comparisons between individual treatments and co-administrations). Statistical analyses were performed using a 1-way ANOVA (analysis of variance) followed by a Bonferroni multiple comparison test with the overall alpha set at 0.05. In Tables 1 and 2, asterisks (*) denote significant effects compared to vehicle-treated rats, while letters (a or b) denote significant effects compared to rats treated with a single compound ("a" for significance from antidepressant and "b" for significance from telenzepine). In Tables 1 and 2, one symbol denotes p<0.05, two symbols denote p<0.01 and three symbols denote p<0.001). The symbols used for denoting statistical significance may be different in the corresponding figures.

TABLE 1

| | | 4 Hr Consumption | | | |
|---|---|---|---|---|---|
| Compound | Dose (mg/kg) | Vehicle Consumption (g/4 Hrs) | Treatment Consumption (g/4 Hrs) | % Reduction in Consumption | p Values |
| Citalopram | 25 (ip)$^a$ | 7.6 ± 0.44 | 5.3 ± 0.72 | 31% | * |
| Sertraline | 10 (ip)$^a$ | 7.6 ± 0.44 | 6.0 ± 0.88 | 21% | n.s |
| | 30 (ip)$^a$ | 7.6 ± 0.44 | 5.6 ± 0.73 | 27% | * |
| Venlafaxine | 30 (ip)$^b$ | 7.0 ± 0.51 | 6.1 ± 0.84 | 13% | n.s. |
| Telenzepine | 1 (ip)$^b$ | 7.0 ± 0.51 | 4.0 ± 0.50 | 43% | *** |
| | 1 (ip)$^e$ | 9.2 ± 1.09 | 5.7 ± 0.63 | 38% | ** |
| | 3 (ip)$^b$ | 7.0 ± 0.51 | 4.5 ± 0.40 | 35% | *** |
| | 3 (ip)$^a$ | 7.6 ± 0.44 | 4.2 ± 0.36 | 45% | *** |
| | 3 (ip)$^e$ | 9.2 ± 1.09 | 5.5 ± 0.60 | 40% | ** |
| | 10 (ip)$^e$ | 9.2 ± 1.09 | 4.1 ± 0.55 | 56% | ** |
| | 10 (po)$^c$ | 10.3 ± 1.05 | 7.4 ± 0.64 | 28% | n.s. |
| | 30 (po)$^c$ | 10.3 ± 1.05 | 6.6 ± 1.01 | 36% | n.s. |
| Sibutramine | 1 (po)$^c$ | 10.3 ± 1.05 | 10.1 ± 1.24 | 0% | n.s |
| | 1 (po)$^d$ | 6.8 ± 1.09 | 4.9 ± 0.68 | 28% | n.s. |
| | 3 (po)$^c$ | 10.3 ± 1.05 | 8.0 ± 1.29 | 23% | n.s. |
| | 3 (po)$^d$ | 6.8 ± 1.09 | 3.2 ± 0.33 | 54% | ** |
| | 10 (po)$^d$ | 6.8 ± 1.09 | 4.3 ± 0.61 | 38% | * |

TABLE 1-continued

4 Hr Consumption

| Compound | Dose (mg/kg) | Vehicle Consumption (g/4 Hrs) | Treatment Consumption (g/4 Hrs) | % Reduction in Consumption | p Values |
|---|---|---|---|---|---|
| Venlafaxine + Telenzepine | 30 + 1 (ip)[b] | 7.0 ± 0.51 | 2.7 ± 0.48 | 62% | ***, a, b |
|  | 30 + 3 (ip)[b] | 7.0 ± 0.51 | 3.0 ± 0.34 | 56% | ***, aa, bb |
| Citalopram + Telenzepine | 25 + 3 (ip)[a] | 7.6 ± 0.44 | 2.0 ± 0.15 | 73% | ***, aaa, b |
| Sertraline + Telenzepine | 10 + 3 (ip)[a] | 7.6 ± 0.44 | 2.4 ± 0.29 | 69% | ***, aaa |
|  | 30 + 3 (ip)[a] | 7.6 ± 0.44 | 2.0 ± 0.42 | 73% | ***, aaa, b |
| Sibutramine + Telenzepine | 1 + 30 (po)[c] | 10.3 ± 1.05 | 4.8 ± 0.93 | 53% | **, aa |

TABLE 2

24 Hr Consumption

| Compound | Dose (mg/kg) | Vehicle Consumption (g/24 Hrs) | Treatment Consumption (g/24 Hrs) | % Reduction in Consumption | p Values |
|---|---|---|---|---|---|
| Citalopram | 25 (ip)[a] | 23.9 ± 0.91 | 23.0 ± 0.71 | 4% | n.s. |
| Sertraline | 10 (ip)[a] | 23.9 ± 0.91 | 23.5 ± 0.71 | 2% | n.s. |
|  | 30 (ip)[a] | 23.9 ± 0.91 | 17.1 ± 1.60 | 28% | *** |
| Venlafaxine | 30 (ip)[b] | 25.0 ± 1.03 | 24.9 ± 1.52 | 0% | n.s. |
| Telenzepine | 1 (ip)[b] | 25.0 ± 1.03 | 20.9 ± 0.78 | 16% | *** |
|  | 1 (ip)[e] | 28.9 ± 1.16 | 23.6 ± 1.01 | 18% | * |
|  | 3 (ip)[b] | 25.0 ± 1.03 | 19.4 ± 0.94 | 22% | *** |
|  | 3 (ip)[a] | 23.9 ± 0.91 | 17.5 ± 1.38 | 27% | ** |
|  | 3 (ip)[e] | 28.9 ± 1.16 | 19.7 ± 0.95 | 32% | ** |
|  | 10 (ip)[e] | 28.9 ± 1.16 | 14.5 ± 1.29 | 50% | ** |
|  | 10 (po)[c] | 30.3 ± 1.54 | 18.5 ± 2.33 | 39% | ** |
|  | 30 (po)[c] | 30.3 ± 1.54 | 13.3 ± 2.69 | 56% | *** |
| Sibutramine | 1 (po)[c] | 30.3 ± 1.54 | 27.4 ± 1.78 | 10% | n.s. |
|  | 1 (po)[d] | 24.7 ± 0.89 | 20.7 ± 1.05 | 16% | * |
|  | 3 (po)[c] | 30.3 ± 1.54 | 21.9 ± 1.98 | 28% | * |
|  | 3 (po)[d] | 24.7 ± 0.89 | 15.4 ± 1.22 | 38% | ** |
|  | 10 (po)[d] | 24.7 ± 0.89 | 11.9 ± 1.15 | 52% | ** |
| Venlafaxine + Telenzepine | 30 + 1 (ip)[b] | 25.0 ± 1.03 | 17.1 ± 1.68 | 31% | ***, a, b |
|  | 30 + 3 (ip)[b] | 25.0 ± 1.03 | 15.5 ± 1.18 | 38% | ***, aa, bb |
| Citalopram + Telenzepine | 25 + 3 (ip)[a] | 23.9 ± 0.91 | 9.5 ± 1.23 | 60% | ***, aaa, bbb |
| Sertraline + Telenzepine | 10 + 3 (ip)[a] | 23.9 ± 0.91 | 12.6 ± 1.27 | 47% | ***, aaa, b |
|  | 30 + 3 (ip)[a] | 23.9 ± 0.91 | 8.8 ± 1.33 | 63% | ***, aaa, bbb |
| Sibutramine + Telenzepine | 1 + 30 (po)[c] | 30.3 ± 1.54 | 11.2 ± 1.51 | 63% | ***, aaa |

Figure 6:
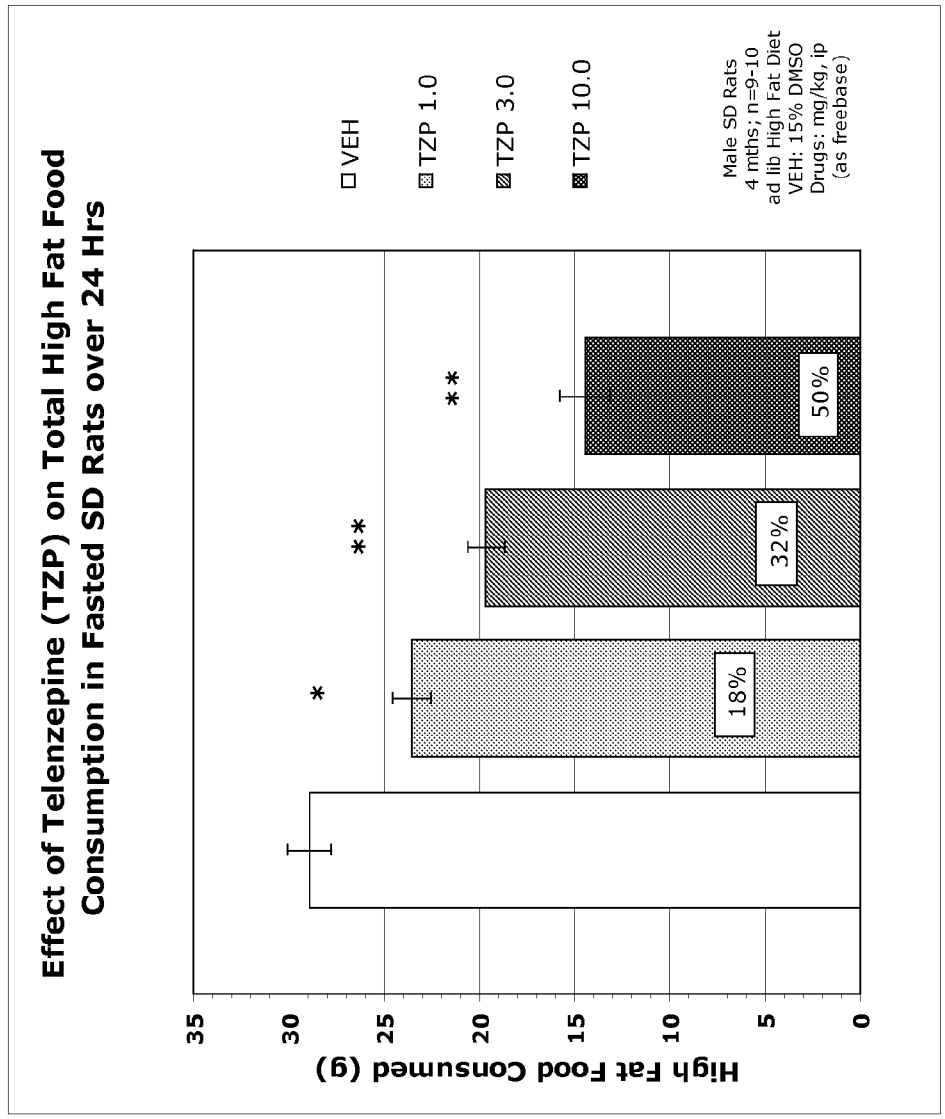
FIG. 6 illustrates the effect of telenzepine (TZP) on total high fat food consumption in fasted rats over 24 hours. Four-month old male Sprague-Dawley rats (n=9-10 per group) were administered intraperitoneally telenzepine in doses of 1.0 mg/kg, 3.0 mg/kg or 10.0 mg/kg, as described in the Examples below. All active agents were delivered in free base form. Control rats (VEH) were administered 15% DMSO. * indicates p<0.05 vs. VEH. ** indicates p<0.01 vs. VEH.
Figure 7:
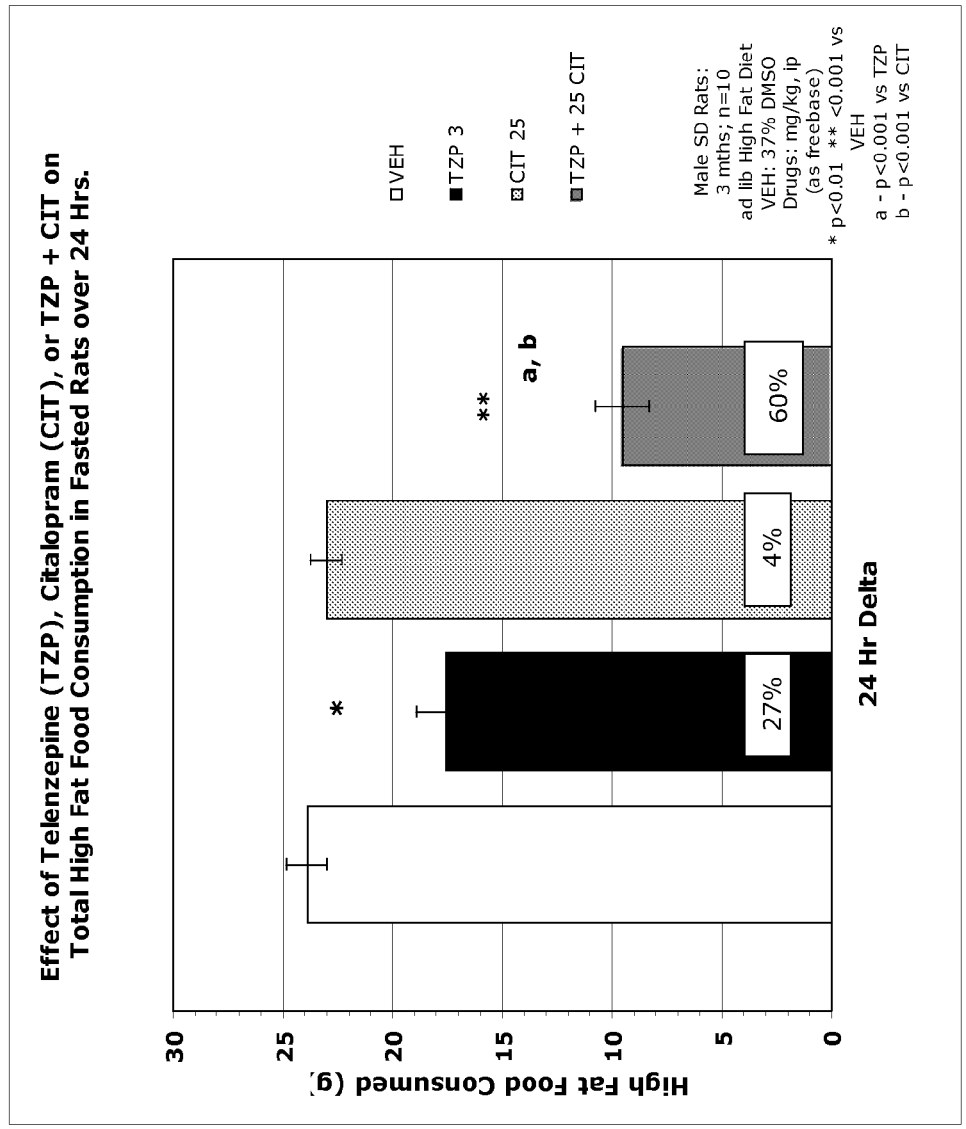
FIG. 7 illustrates the effect of telenzepine (TZP) alone, citalopram (CIT) alone and combined telenzepine and citalopram on total high fat food consumption in fasted rats over 24 hours. Three-month old male Sprague-Dawley rats (n=10 per group) were administered intraperitoneally telenzepine alone (3 mg/kg), citalopram alone (25 mg/kg), or co-administered telenzepine (3 mg/kg) and citalopram (25 mg/kg), as described in the Examples below. All active agents were delivered in free base form. Control rats (VEH) were administered 37% DMSO. * indicates p<0.01 vs. VEH. ** indicates p<0.001 vs. VEH. "a" indicates p<0.001 vs. TZP. "b" indicates p<0.001 vs. CIT.
Figure 8:
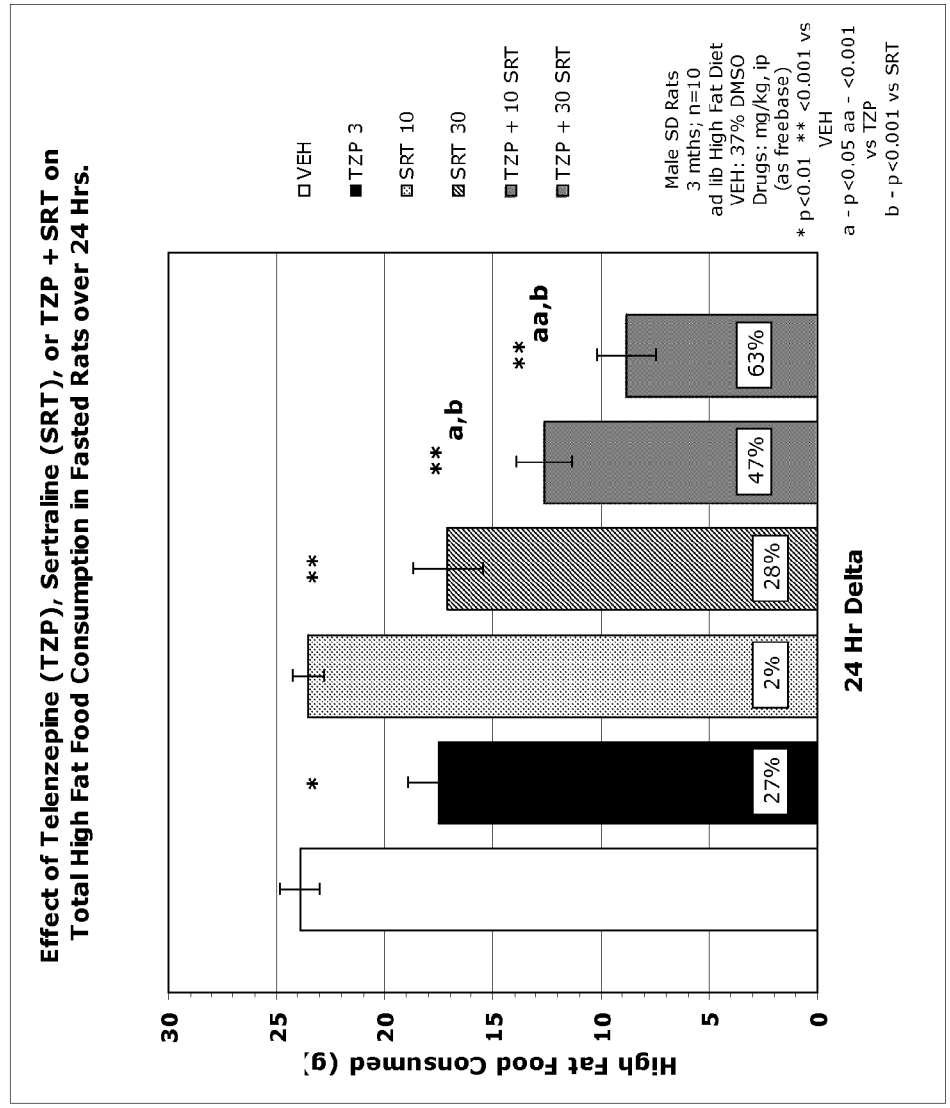
FIG. 8 illustrates the effect of telenzepine (TZP) alone, sertraline (SRT) alone and combined telenzepine and sertraline on total high fat food consumption in fasted rats over 24 hours. Three-month old male Sprague-Dawley rats (n=10 per group) were administered intraperitoneally telenzepine alone (3 mg/kg), sertraline alone (10 mg/kg or 30 mg/kg), or co-administered telenzepine (3 mg/kg) and sertraline (10 mg/kg or 30 mg/kg), as described in the Examples below. All active agents were delivered in free base form. Control rats (VEH) were administered 37% DMSO. * indicates p<0.01 vs. VEH. ** indicates p<0.001 vs. VEH. "a" indicates p<0.05 vs. TZP. "aa" indicates p<0.001 vs. TZP. "b" indicates p<0.001 vs. SRT.
Figure 9:
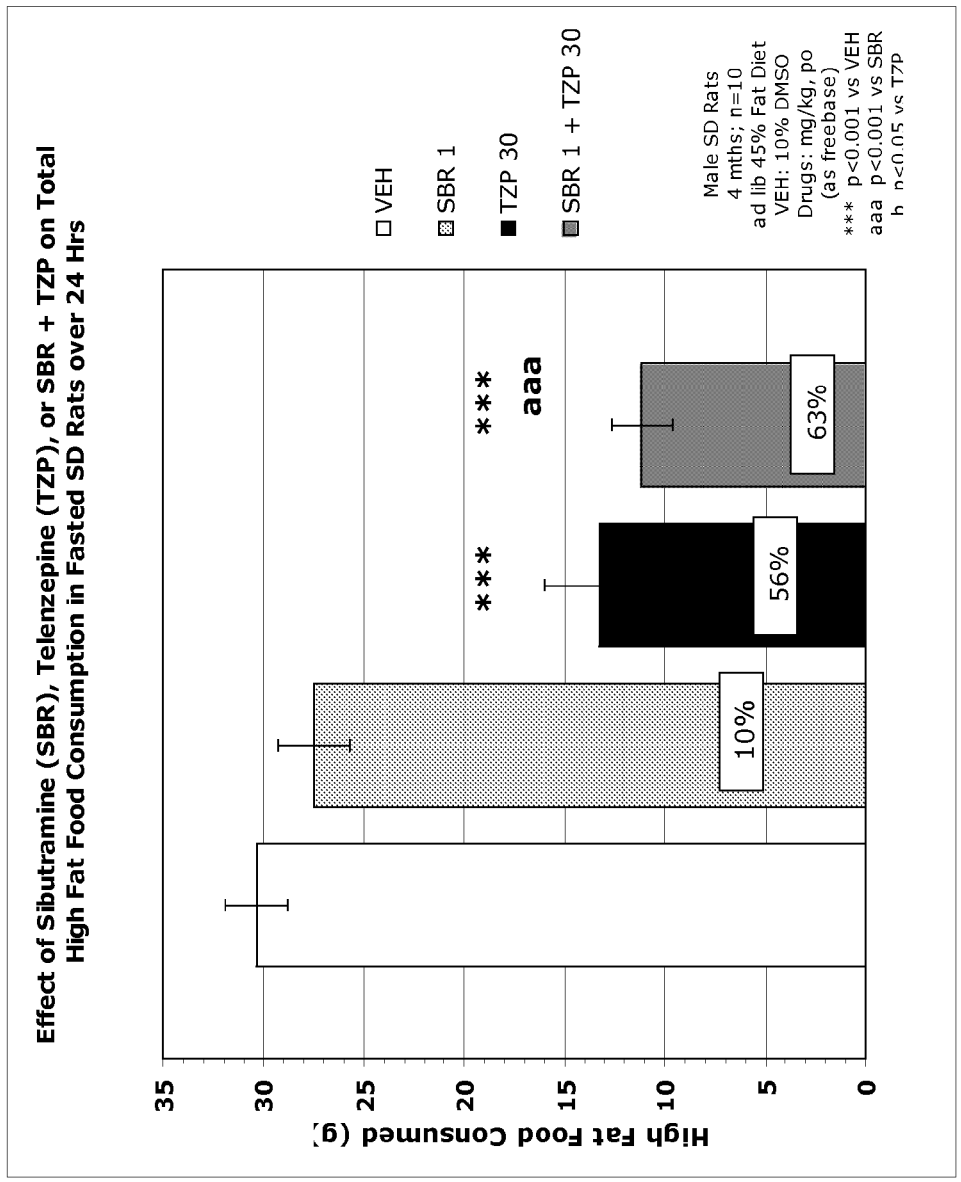
FIG. 9 illustrates the effect of telenzepine (TZP) alone, sibutramine (SBR) alone and combined telenzepine and sibutramine on total high fat food consumption in fasted rats over 24 hours. Four-month old male Sprague-Dawley rats (n=10 per group) were administered orally telenzepine alone (30 mg/kg), sibutramine alone (1.0 mg/kg), or co-administered telenzepine (30 mg/kg) and sibutramine (1.0 mg/kg), as described in the Examples below. All active agents were delivered in free base form. Control rats (VEH) were administered 10% DMSO. *** indicates $p<0.001$ vs. VEH. "aaa" indicates $p<0.001$ vs. SBR.
Figure 10:
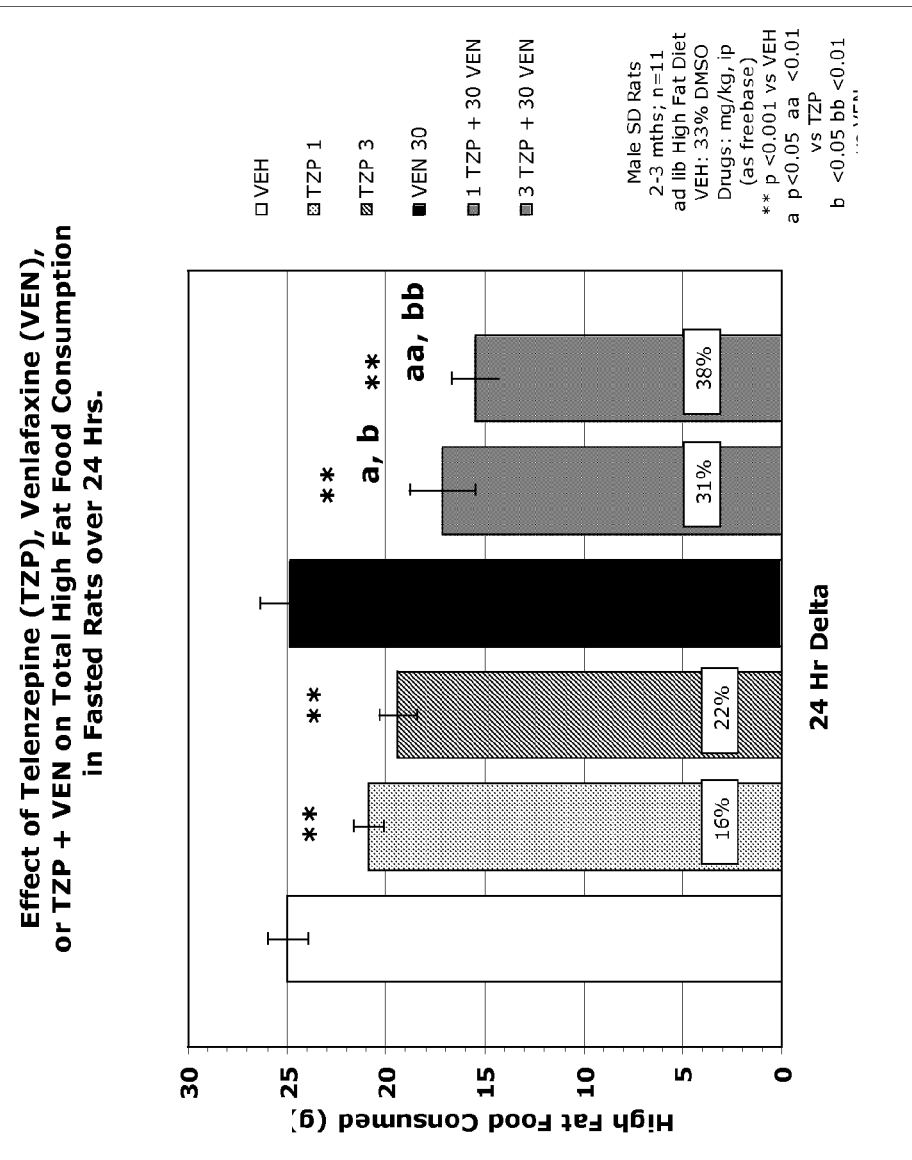
FIG. 10 illustrates the effect of telenzepine (TZP) alone, venlafaxine (VEN) alone and combined telenzepine and venlafaxine on total high fat food consumption in fasted rats over 24 hours. Two/Three-month old male Sprague-Dawley rats (n=11 per group) were administered intraperitoneally telenzepine alone (1 mg/kg or 3 mg/kg), venlafaxine alone (30 mg/kg), or co-administered telenzepine (1 mg/kg or 3 mg/kg) and venlafaxine (30 mg/kg), as described in the Examples below. All active agents were delivered in free base form. Control rats (VEH) were administered 33% DMSO. ** indicates $p<0.001$ vs. VEH. "a" indicates $p<0.05$ vs. TZP. "aa" indicates $p<0.01$ vs. TZP. "b" indicates $p<0.05$ vs. VEN. "bb" indicates $p<0.01$ vs. VEN.
Figure 11:
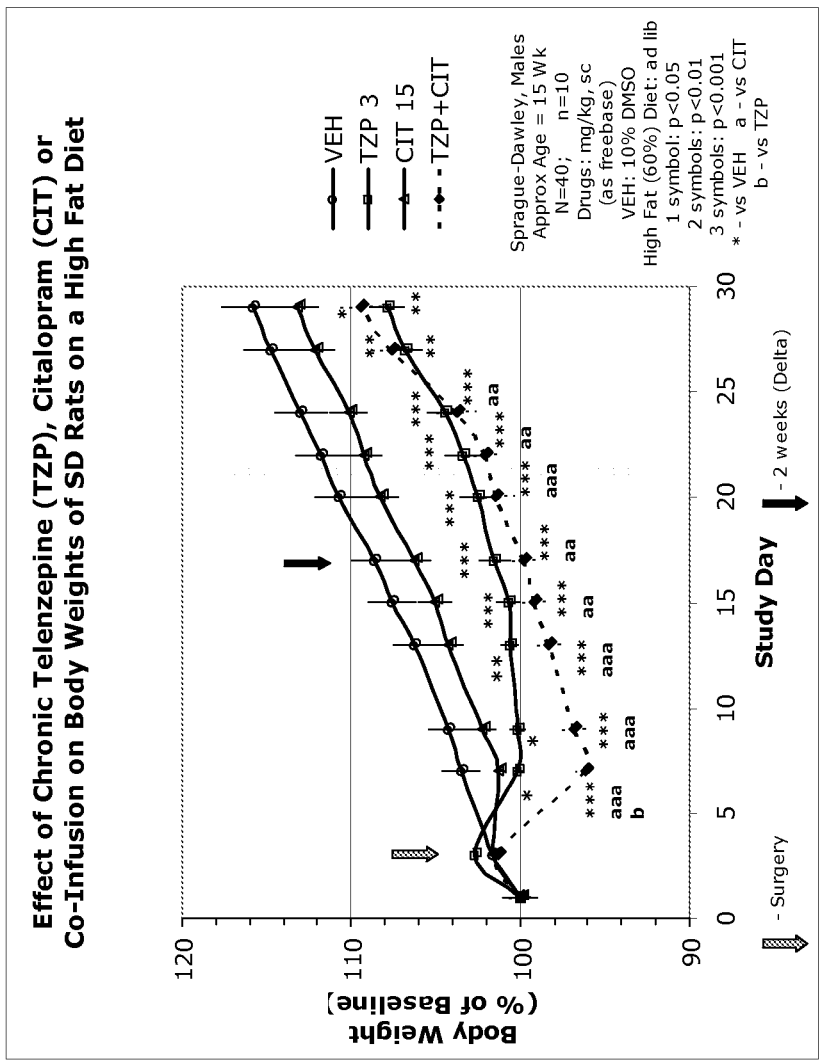
FIG. 11 illustrates the effect of chronic administration of telenzepine (TZP), citalopram (CIT) and combined telenzepine and citalopram on body weights of rats on a high fat diet. Approximately fifteen-week old male Sprague-Dawley rats (n=10 per group) received subcutaneous infusion of telenzepine alone (3 mg/kg), citalopram alone (15 mg/kg), or co-administered telenzepine (3 mg/kg) and citalopram (15 mg/kg), as described in the Examples below. All active agents were delivered in free base form. Control rats (VEH) were administered 10% DMSO. * indicates $p<0.05$ vs. VEH.  indicates $p<0.01$ vs. VEH. * indicates $p<0.001$ vs. VEH. "aa" indicates $p<0.01$ vs. CIT. "aaa" indicates $p<0.001$ vs. CIT. "b" indicates $p<0.05$ vs. TZP. The shaded area indicates the treatment interval.
Figure 12:
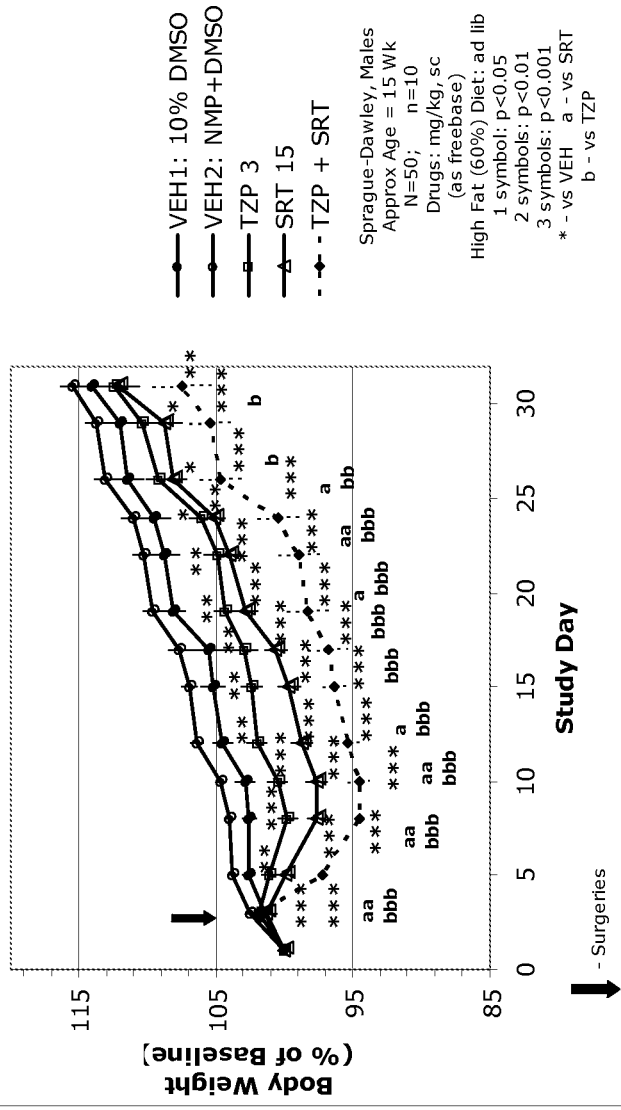
FIG. 12 illustrates the effect of chronic administration of telenzepine (TZP), sertraline (SRT) and combined telenzepine and sertraline on body weights of rats on a high fat diet. Approximately fifteen-week old male Sprague-Dawley rats (n=10 per group) received subcutaneous infusion of telenzepine alone (3 mg/kg), sertraline alone (15 mg/kg), or co-administered telenzepine (3 mg/kg) and sertraline (15 mg/kg), as described in the Examples below. All active agents were delivered in free base form. Control rats were administered 10% DMSO (VEH1) or N-methyl-2-pyrrolidone+DMSO+water (1:2:2) ("NMP:DMSO:water" or VEH2). * indicates $p<0.05$ vs. VEH.  indicates $p<0.01$ vs. VEH. * indicates $p<0.001$ vs. VEH. "a" indicates $p<0.05$ vs. SRT. "aa" indicates $p<0.01$ vs. SRT. "aaa" indicates $p<0.001$ vs. SRT. "b" indicates $p<0.05$ vs. TZP. "bb" indicates $p<0.01$ vs. TZP. "bbb" indicates $p<0.001$ vs. TZP. The shaded area indicates the treatment interval.
Figure 13:
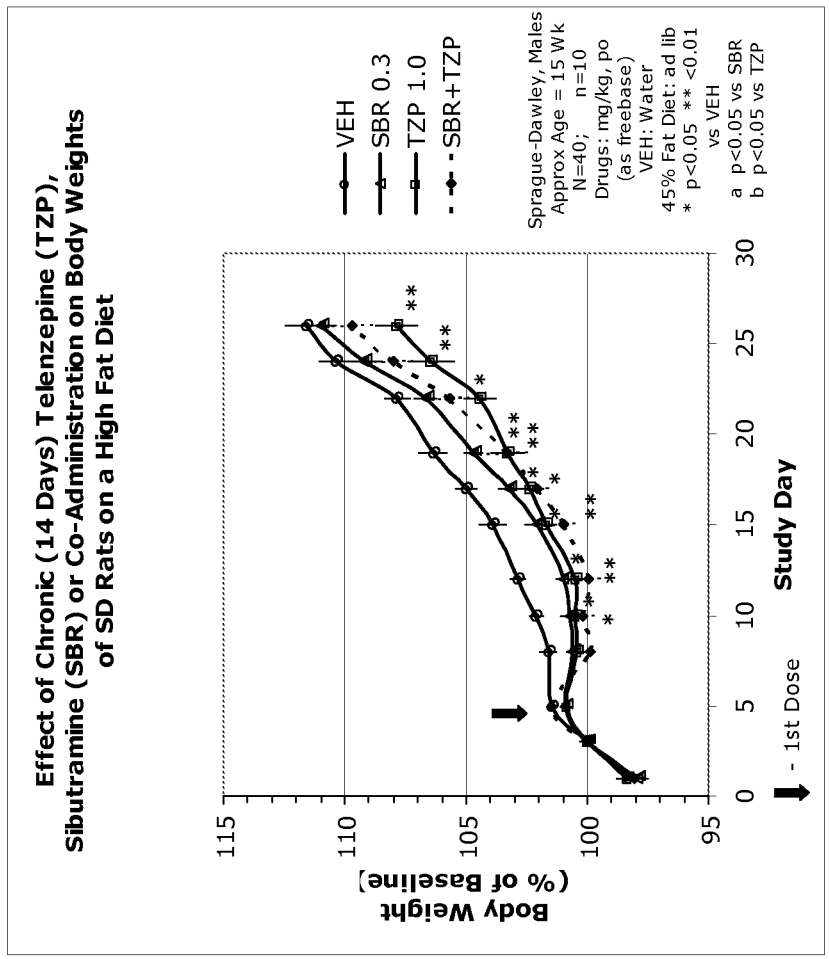
FIG. 13 illustrates the effect of chronic administration of telenzepine (TZP), sibutramine (SBR) and combined telenzepine and sibutramine on body weights of rats on a high fat diet. Approximately fifteen-week old male Sprague-Dawley rats (n=10 per group) were administered orally telenzepine alone (1.0 mg/kg), sibutramine alone (0.3 mg/kg), or co-administered telenzepine (1.0 mg/kg) and sibutramine (0.3 mg/kg), as described in the Examples below. All active agents were delivered in free base form. Control rats (VEH) were administered water. * indicates $p<0.05$ vs. VEH. ** indicates $p<0.01$ vs. VEH. "a" indicates $p<0.05$ vs. SBR. "b" indicates $p<0.05$ vs. TZP. The shaded area indicates the treatment interval.
Figure 14:
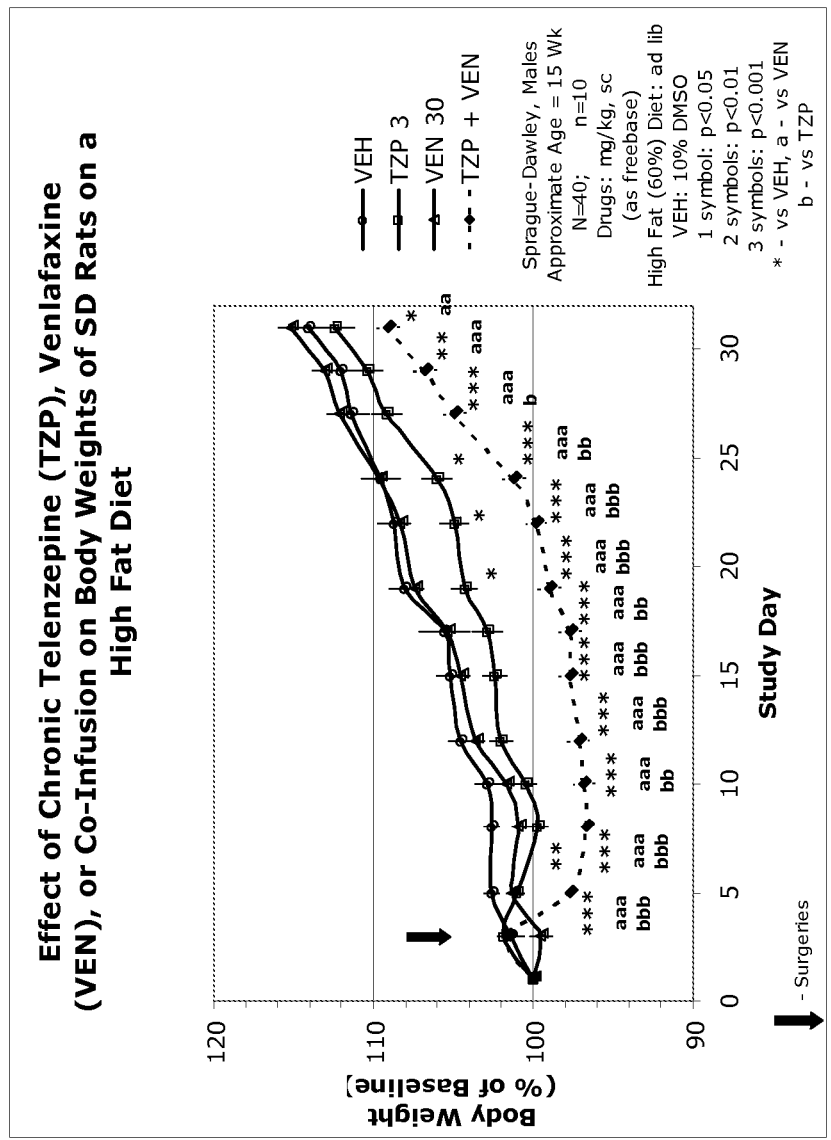
FIG. 14 illustrates the effect of chronic administration of telenzepine (TZP), venlafaxine (VEN) and combined telenzepine and venlafaxine on body weights of rats on a high fat diet. Approximately fifteen-week old male Sprague-Dawley rats (n=10 per group) received subcutaneous infusion of telenzepine alone (3 mg/kg), venlafaxine alone (30 mg/kg), or co-administered telenzepine (3 mg/kg) and venlafaxine (30 mg/kg), as described in the Examples below. All active agents were delivered in free base form. Control rats (VEH) were administered 10% DMSO. * indicates $p<0.05$ vs. VEH.  indicates $p<0.01$ vs. VEH. * indicates $p<0.001$ vs. VEH. "a" indicates $p<0.05$ vs. VEN. "aa" indicates $p<0.01$ vs. VEN. "aaa" indicates $p<0.001$ vs. VEN. "b" indicates $p<0.05$ vs. TZP. "bb" indicates $p<0.01$ vs. TZP. "bbb" indicates $p<0.001$ vs. TZP. The shaded area indicates the treatment interval.
Figure 15:
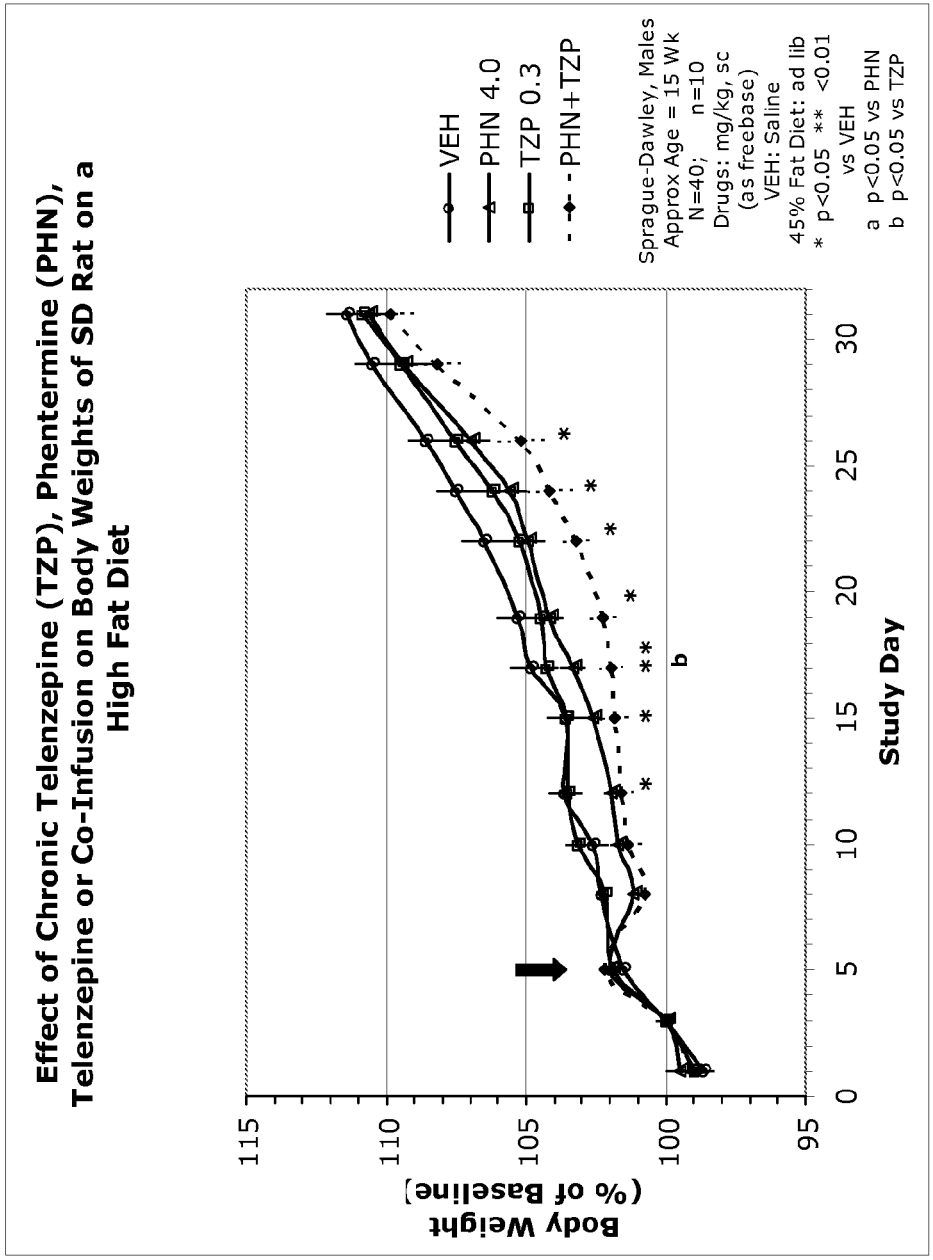
FIG. 15 illustrates the effect of chronic administration of telenzepine (TZP), phentermine (PHN) and combined telenzepine and phentermine on body weights of rats on a high fat diet. Approximately fifteen-week old male Sprague-Dawley rats (n=10 per group) received subcutaneous infusion of telenzepine alone (0.3 mg/kg), phentermine alone (4.0 mg/kg), or co-administered telenzepine (0.3 mg/kg) and phentermine (4.0 mg/kg), as described in the Examples below. All active agents were delivered in free base form. Control rats (VEH) were administered saline. * indicates $p<0.05$ vs. VEH. ** indicates $p<0.01$ vs. VEH. "a" indicates $p<0.05$ vs. PHN. "b" indicates $p<0.05$ vs. TZP. The shaded area indicates the treatment interval.

Note on Effects:

24-hour consumption effects better reflect the sustained duration of action and are better exemplars of anorectic effects than are the 4-hour consumption effects. All doses of telenzepine tested (ip) significantly reduced consumption when given alone (FIGS. 1 and 6). Also, after 24 hours nearly all combinations resulted in reductions in consumption that were greater than predicted from mere additivity.

For example, 25 mg/kg of citalopram produced a modest reduction in consumption over 4 hours (31%, p<0.05), but was essentially without effect over 24 hours (4%, n.s.). 3 mg/kg of telenzepine produced a larger reduction in consumption over 4 hours (45%, p<0.001), which was still significant over 24 hours (27%, p<0.01). Co-administration of these compounds produced a significant reduction in consumption over 4 hours (73%, p<0.001) and 24 hours (60%, p<0.001) (see FIGS. 2 and 7 for 4-hr and 24-hr effects, respectively). The magnitude of the 24 hour effect is indicative of synergy as it is greater than what would be expected from additive effects.

In another example, 30 mg/kg of venlafaxine produced a non-significant reduction in consumption over 4 hours (13%), and was essentially without effect over 24 hours (0%, n.s.). 3 mg/kg of telenzepine produced a larger reduction in consumption over 4 hours (35%, p<0.001), which was still significant over 24 hours (22%, p<0.001). Co-administration of these compounds produced a significant reduction in consumption over 4 hours (56%, p<0.001) and 24 hours (38%, p<0.001) (see FIGS. 5 and 10 for 4-hr and 24-hr effects, respectively). The magnitude of both the 4 hour and the 24 hour effects are indicative of synergy as they are greater than what would be expected from additive effects. Similarly, co-administration of a lower dose of telenzepine (1 mg/kg) with 30 mg/kg of venlafaxine also resulted in synergistic effects on consumption over both intervals.

In a further example, 30 mg/kg of sertraline produced a modest reduction in consumption over 4 hours (27%, p<0.05), that was maintained over 24 hours (28%, p<0.001), while the lower dose (10 mg/kg) displayed lessened efficacy and duration (non-significant reductions of 21% and 2% over 4 hours and 24 hours, respectively). 3 mg/kg of telenzepine produced a larger reduction in consumption over 4 hours (45%, p<0.001), which was still significant over 24 hours (27%, p<0.01). Co-administration of telenzepine and the "high dose" of sertraline produced a significant reduction in consumption over 4 hours (73%, p<0.001) and 24 hours (63%, p<0.001). Likewise, co-administration of telenzepine and the "low dose" of sertaline produced a significant reduction in consumption over 4 hours (69%, p<0.001) and 24 hours (47%, p<0.001) (see FIGS. 3 and 8 for 4-hr and 24-hr effects, respectively). The magnitude of both the 4 hour and the 24 hour effects are indicative of synergy as they are greater than what would be expected from additive effects.

In nearly all combinations of the present example, reductions produced by the combinations are significantly different from not only vehicle treated rats, but also from the effect of either compound given alone. In nearly all combinational experiments, consumption was reduced by greater than 50% over both intervals. The clinical reference, sibutramine, was also effective when given alone, although oral administration was required to produce a significant reduction (ip data not given). Additionally, when 30 mg/kg of telenzepine was co-administered, the effective dose of sibutramine could be lowered to 1 mg/kg, representing a 3-fold (4 hour consumption) to 10-fold (24 hour consumption) reduction in dose.

Example 2

Reduction in Weight Gain: Three- to four-month-old (475-550 grams) male, Sprague-Dawley rats (individually housed) were used to assess compounds for their ability to prevent weight gain. At the onset of chronic experiments, rats had been maintained (ad libitum access) on a "high fat" diet (BioServ Diet #F3282 or Research Diets #12451) for approximately one month. Individual body weights and water consumptions were recorded three times per week throughout the duration of the experiment. After approximately two weeks of data collection, rats were counter-balanced to produce treatment groups with equivalent mean body weights. Under isofluorane-induced anesthesia, rats were surgically implanted (subscapular, subcutaneous [sc] placement) with osmotic mini-pumps (Alzet 2mL2) containing the appropriate drug concentration (based on mean body weights and calculated durations of delivery). Alternatively, for studies using the oral route of administration, rats were dosed by gavage daily over 14 days at a volume of 3 mL/kg. Data collection was continued under drug treatment for approximately two more weeks. Change in body weight (expressed in grams) was calculated for the treatment interval. In this assay, vehicle-treated rats typically gain approximately 35-40 grams (+9%) over the two-week interval. Treatment effects are presented in Table 3 as % Weight Gain=[(Body Weight at End of Drug Infusion−Baseline Body Weight)/Baseline Body Weight]×100%, for both Vehicle and Treatment groups; as well as % Reduction=(% Weight Gain for Treatment group−% Weight Gain for Vehicle group). Body weights throughout the treatment period are presented in FIGS. 11-15 as the percentage of baseline body weight. Similar superscripts in the Dose column of Table 3 denote values derived from the same experiment (to facilitate comparisons between individual treatments and co-administrations). Statistical analyses were performed using a 1-way ANOVA (analysis of variance) followed by a Bonferroni multiple comparison test with the overall alpha set at 0.05. In Table 3, asterisks (*) denote significant effects compared to vehicle-treated rats, while letters (a or b) denote significant effects compared to rats treated with a single compound ("a" for significance from antidepressant and "b" for significance from telenzepine). In Table 3, one symbol denotes p<0.05, two symbols denote p<0.01 and three symbols denote p<0.001). The symbols used for denoting statistical significance may be different in the corresponding figures.

TABLE 3

| Compound | Dose (mg/kg) | Vehicle: % Weight Gain | Treatment: % Weight Gain | % Reduction | p Values |
|---|---|---|---|---|---|
| Citalopram | 15 (sc)$^a$ | 8.6 ± 1.4% | 6.2 ± 1.0% | −2.4% | n.s. |
| Sertraline | 5 (sc) | 9.3 ± 0.3% | 7.2 ± 1.2% | −2.1% | n.s. |
|  | 10 (sc) | 9.1 ± 0.7% | 6.0 ± 0.8% | −3.1% | ** |
|  | 15 (sc)$^b$ | 9.6 ± 0.7% | 2.8 ± 0.8% | −6.8% | *** |
|  | 20 (sc) | 6.3 ± 0.4% | 2.8 ± 0.7% | −3.5% | * |
| Venlafaxine | 30 (sc)$^b$ | 8.1 ± 0.8% | 7.4 ± 0.5% | −0.7% | n.s. |
| Phentermine | 4 (sc)$^c$ | 5.3 ± 0.8% | 4.2 ± 0.6% | −1.1% | n.s. |
| Telenzepine | 0.3 (sc)$^c$ | 5.3 ± 0.8% | 4.4 ± 0.6% | −0.9% | n.s. |
|  | 1 (po)$^d$ | 6.4 ± 0.5% | 3.3 ± 0.6% | −3.1% | ** |
|  | 3 (sc)$^b$ | 8.1 ± 0.8% | 4.3 ± 0.8% | −3.8% | * |
|  | 3 (sc)$^a$ | 8.6 ± 1.4% | 1.5 ± 1.0% | −7.1% | *** |
| Sibutramine | 0.3 (po)$^d$ | 6.4 ± 0.5% | 4.7 ± 0.5% | −1.7% | n.s. |
|  | 3 (po) | 0.3 ± 0.9% | −5.7 ± 1.2% | −6.0% | *** |
| Citalopram + Telenzepine | 15 + 3 (sc)$^a$ | 8.6 ± 1.4% | −0.2 ± 1.1% | −8.8% | ***, aa |
| Sertraline + Telenzepine | 15 + 3 (sc)$^b$ | 9.6 ± 0.7% | −1.7 ± 1.6% | −11.3% | ***, aaa, b |
| Venlafaxine + Telenzepine | 30 + 3 (sc)$^b$ | 8.1 ± 0.8% | −1.0 ± 1.1% | −9.1% | ***, aaa, bbb |
| Phentermine + Telenzepine | 4 + 0.3 (sc)$^c$ | 5.3 ± 0.8% | 2.3 ± 0.7% | −3.0% | ** |
| Sibutramine + Telenzepine | 0.3 + 1 (po)$^d$ | 6.4 ± 0.5% | 3.3 ± 0.8% | −3.1% | ** |
| Citalopram | 15 (sc)$^a$ | 8.6 ± 1.4% | 6.2 ± 1.0% | −2.4% | n.s. |
| Sertraline | 5 (sc) | 9.3 ± 0.3% | 7.2 ± 1.2% | −2.1% | n.s. |
|  | 10 (sc) | 9.1 ± 0.7% | 6.0 ± 0.8% | −3.1% | ** |
|  | 15 (sc)$^b$ | 9.6 ± 0.7% | 2.8 ± 0.8% | −6.8% | *** |
|  | 20 (sc) | 6.3 ± 0.4% | 2.8 ± 0.7% | −3.5% | * |

Note on Effects:

Telenzepine given alone (po or sc) significantly reduced the weight gain of rats on a high fat diet when compared against vehicle treated controls (3% to 7% reduction from baseline) (see FIGS. 11-15). The clinical reference compound, sibutramine, also significantly reduced weight gain when compared against vehicle treated controls (6% reduction from baseline) (see FIG. 13). Additionally, sertraline at higher doses (10 and 15 mg/kg, but not 5 mg/kg) also significantly reduced weight gain when compared against vehicle treated controls (3% to 7% reductions from baseline) (see FIG. 12). All other compounds/doses used in the combination studies produced no effect on body weights when given alone.

Combinations of sertraline+telenzepine and venlafaxine+telenzepine produced reductions in body weight that were synergistic and significantly greater than observed with not only vehicle treatment, but also than observed with either compound alone.

In the case of sertraline+telenzepine (FIG. 12), 15 mg/kg of sertraline alone produced a significant reduction (6.8%, $p<0.001$) in body weight compared to vehicle treated rats, and 3 mg/kg of telenzepine alone also produced a significant reduction (3.8%, $p<0.05$) in body weight compared to vehicle treated rats. However, co-administration of sertraline and telenzepine at these same doses resulted in an 11.3% reduction from baseline that was significant compared to not only vehicle treatment ($p<0.001$) but also treatment with sertraline alone ($p<0.001$) or telenzepine alone ($p<0.05$).

In the case of venlafaxine+telenzepine (FIG. 14), 30 mg/kg of venlafaxine alone failed to produced a significant reduction (0.7%) in body weight compared to vehicle treated rats, while 3 mg/kg of telenzepine alone produced a significant reduction (3.8%, $p<0.05$) in body weight compared to vehicle treated rats. However, co-administration of venlafaxine and telenzepine at these same doses resulted in a 9.1% reduction from baseline that was significant compared to not only vehicle treatment ($p<0.001$) but also treatment with venlafaxine alone ($p<0.001$) or telenzepine alone ($p<0.001$). In both above examples, synergistic effects are evidenced by the increased magnitude of total reduction in body weights under co-administration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for promoting weight loss or facilitating maintenance of a stable weight, the method comprising co-administering to an obese or overweight human individual in need thereof telenzepine and sertraline for at least 80 days to effectuate weight loss, wherein the telenzepine is administered at a dose of about 0.5 mg per day to about 10 mg per day and the sertraline is administered at a dose of about 50 mg per day to about 200 mg per day, whereby weight loss is promoted or maintenance of a stable weight is facilitated.

2. The method of claim 1, wherein the telenzepine and the sertraline are administered concurrently.

3. The method of claim 2, wherein the telenzepine and the sertraline are administered as an admixture.

4. The method of claim 1, wherein the telenzepine and the sertraline are administered sequentially.

5. The method of claim 1, wherein the telenzepine is administered at a dose of about 1 mg per day to about 5 mg per day.

6. The method of claim 1, wherein the sertraline is administered at a dose of about 100 mg per day to about 150 mg per day.

7. The method of claim 1, wherein the telenzepine is administered with a meal.

8. The method of claim 1, wherein one or both of the telenzepine and the sertraline are administered in a sustained-release formulation.

9. The method of claim 1, wherein the telenzepine and the sertraline are co-administered for at least 150 days.

10. The method of claim 1, wherein the telenzepine and the sertraline are co-administered for at least 200 days.

* * * * *